United States Patent [19]

Bechtel et al.

[11] Patent Number: 4,926,350

[45] Date of Patent: May 15, 1990

[54] NON-DESTRUCTIVE TESTING METHODS FOR LUMBER

[75] Inventors: Friend K. Bechtel, Moscow, Id.; James R. Allen, Pullman, Wash.

[73] Assignee: Metriguard, Inc., Pullman, Wash.

[21] Appl. No.: 96,922

[22] Filed: Sep. 14, 1987

[51] Int. Cl.$^5$ .................... G01R 27/00; G01N 21/00; B07C 5/14

[52] U.S. Cl. ................. 364/550; 364/474.09; 73/432.1; 209/517; 250/563; 356/445

[58] Field of Search .................. 364/550, 478, 474.09, 364/474.13; 324/58.5 R, 61 R; 356/446, 445, 231; 250/559, 562, 563, 572; 73/65, 432.1; 209/517, 521

[56] References Cited

U.S. PATENT DOCUMENTS

| | | | |
|---|---|---|---|
| 3,194,063 | 7/1965 | McKean | 73/789 |
| 3,196,672 | 7/1965 | Keller | 73/812 |
| 3,805,156 | 4/1974 | Norton et al. | 324/61 R |
| 3,942,021 | 3/1976 | Barr et al. | 364/474.13 X |
| 3,976,384 | 8/1976 | Matthews et al. | 250/563 X |
| 4,017,976 | 4/1977 | Barr et al. | 364/474.13 X |
| 4,195,346 | 3/1980 | Schröder | 364/474.13 X |
| 4,207,472 | 6/1980 | Idelsohn et al. | 250/563 |
| 4,221,974 | 9/1980 | Mueller et al. | 364/474.13 X |
| 4,372,163 | 2/1983 | Tittmann et al. | 364/550 X |
| 4,500,835 | 2/1985 | Heikkila | 324/58.5 R |
| 4,514,816 | 4/1985 | Ollus et al. | 364/478 |
| 4,606,645 | 8/1986 | Matthews et al. | 356/446 |
| 4,607,212 | 8/1986 | Jakkula | 324/58.5 R |
| 4,789,820 | 12/1988 | Parrent, Jr. et al. | 324/58.5 R |

OTHER PUBLICATIONS

Cramer, Steven M. and Goodman, James R., 1985, Predicting Tensile Strength of Lumber, *Fifth Nondestructive Testing of Wood Symposium*, WSU, Pullman, Wash., pp. 525–545.

McDonald, Kent and Bendtsen, B. Alan, 1985, Measuring Localized Slope of Grain by Electronic Capacitance, *Forest Prod. J*, 36 (10): 75–76.

McLauchlan, T. A. and Kusec, D. J., 1978, Continuous Non—Contact Slope—of—Grain Detection, *Fourth Nondestructive Testing of Wood Symposium*, WSU Engineering Extension Service Pullman, Wash., Vancouver, Wash., pp. 67–76.

McLauchlan, T. A.; Norton, J. A. and Kusec, D. J., 1973, Slope—of—Grain Indicator, *Forest Prod. J.*, 23(5): 50–55.

Samson, Marcel, 1984, Measuring General Slope of Grain with the Slope of Grain Indicator, *Forest Prod. J.* 34(7/8): 27–32.

McDonald, Kent and Bendtsen, 1985, Localized Slope—of—Grain Its Importance and Measurement, *Fifth Nondestructive Testing of Wood Symposium*, Washington State University, Pullman, Wash., pp. 477–489.

Goodman, James R. and Bodig, Jozsef, 1978, Mathematical Model of the Tension Behavior of Wood with Knots and Cross Grain, *Proceedings, First International Conference on Wood Fracture*, Banff, Alberta, pp. 53–61.

Metriguard Brochure: Grain Slope Measurement with the Metriguard 5100 Slope—of—Grain—Indicator.

Metriguard Brochure: CLT—Continuous Lumber Tester.

*Primary Examiner*—P.S. Lall
*Assistant Examiner*—Joseph L. Dixon
*Attorney, Agent, or Firm*—Wells, St. John & Roberts

[57] ABSTRACT

A non-destructive testing system for lumber involves measurement of grain angle about a board and transformation of the measured grain angle values to extract features indicative of knot identification, grain angle perturbations or strength of the board. Individual boards can then be processed for grading or sorting purposes as a function of the extracted features. Specific features utilized for knot identification are curl, divergence, and novel transformations termed gradient, edges and knots, as well as various pattern matching techniques. Strength estimation involves transformations pertaining to failure distance, which is a function of board tensile strength. Failure distance can be computed by an ellipsoidal model, a search model or a tracks model. When utilized in conjunction with conventional bending test procedures, highly accurate strength estimation is achieved by the described system.

24 Claims, 25 Drawing Sheets $$\theta_e = \tan^{-1}(a/c) \quad \Rightarrow \quad a = c(\tan\theta_e)$$

$$\theta_f = \tan^{-1}(b/c) \quad \Rightarrow \quad b = c(\tan\theta_f)$$

$$\theta_a = \tan^{-1}((a^2+b^2)^{1/2}/c)$$

$$\boxed{\begin{array}{c} \theta_a = \tan^{-1}((\tan^2\theta_e + \tan^2\theta_f)^{1/2}) \\ \theta_a \approx (\theta_e^2 + \theta_f^2)^{1/2} \end{array}}$$

|  | 0 1 2 3 4 5 6 7 8 |  | 0 1 2 3 4 5 6 7 8 |
|---|---|---|---|
| 0 | 0 0 0 0 0 0 0 0 0 | 36 | 0 0 0 0 0 0 0 0 0 |
| 1 | 0 0 0 0 0 0 0 0 0 | 37 | 0 0 0 0 0 0 0 0 0 |
| 2 | 0 0 0 0 0 0 0 0 0 | 38 | 0 0 0 0 0 0 0 0 0 |
| 3 | 0 0 0 0 0 0 0 0 0 | 39 | 0 0 0 0 0 0 0 0 0 |
| 4 | 0 0 0 0 0 0 0 0 0 | 40 | 0 0 0 0 0 0 0 0 0 |
| 5 | 0 0 0 0 0 0 0 0 0 | 41 | 0 0 0 0 0 0 0 0 0 |
| 6 | 0 0 0 0 0 0 0 0 0 | 42 | 0 0 0 0 0 0 0 0 0 |
| 7 | 0 0 0 0 0 0 0 0 0 | 43 | 0 0 0 0 0 0 0 0 0 |
| 8 | 0 0 0 0 0 0 0 0 0 | 44 | 0 0 0 0 0 0 0 0 0 |
| 9 | 0 0 0 0 0 0 0 0 0 | 45 | 0 1 1 1 1 0 0 0 0 |
| 10 | 0 0 0 0 0 0 0 0 0 | 46 | 1 1 2 2 1 1 0 0 0 |
| 11 | 0 0 0 0 0 0 0 0 0 | 47 | 1 2 2 2 1 1 0 0 0 |
| 12 | 0 0 0 0 0 0 0 0 0 | 48 | 1 2 2 2 2 1 0 0 0 |
| 13 | 0 0 0 0 0 0 0 0 0 | 49 | 1 2 2 2 2 1 0 0 0 |
| 14 | 0 0 0 0 0 0 0 0 0 | 50 | 1 1 2 2 1 1 0 0 0 |
| 15 | 0 0 0 0 0 0 0 0 0 | 51 | 0 0 1 1 1 0 0 0 0 |
| 16 | 0 0 0 0 0 0 0 0 0 | 52 | 0 0 0 0 0 0 0 0 0 |
| 17 | 0 0 0 0 0 0 0 0 0 | 53 | 0 0 0 0 0 0 0 0 0 |
| 18 | 0 0 1 1 1 1 0 0 0 | 54 | 0 0 0 0 0 0 0 0 0 |
| 19 | 0 0 1 2 2 1 1 0 0 | 55 | 0 0 0 0 0 0 0 0 0 |
| 20 | 0 0 1 2 2 2 1 0 0 | 56 | 0 0 0 0 0 0 0 0 0 |
| 21 | 0 0 1 2 2 2 1 0 0 | 57 | 0 0 0 0 0 0 0 0 0 |
| 22 | 0 0 1 1 1 1 1 0 0 | 58 | 0 0 0 0 0 0 0 0 0 |
| 23 | 0 0 1 1 1 1 0 0 0 | 59 | 0 0 0 0 0 0 0 0 0 |
| 24 | 0 0 0 0 0 0 0 0 0 | 60 | 0 0 0 0 0 0 0 0 0 |
| 25 | 0 0 0 0 0 0 0 0 0 | 61 | 0 0 0 0 0 0 0 0 0 |
| 26 | 0 0 0 0 0 0 0 0 0 | 62 | 0 0 0 0 0 0 0 0 0 |
| 27 | 0 0 0 0 0 0 0 0 0 | 63 | 0 0 0 0 0 0 0 0 0 |
| 28 | 0 0 0 0 0 0 0 0 0 | 64 | 0 0 0 0 0 0 0 0 0 |
| 29 | 0 0 0 0 0 0 0 0 0 | 65 | 0 0 0 0 0 0 0 0 0 |
| 30 | 0 0 0 0 0 0 0 0 0 | 66 | 0 0 0 0 0 0 0 0 0 |
| 31 | 0 0 0 0 0 0 0 0 0 | 67 | 0 0 0 0 0 0 0 0 0 |
| 32 | 0 0 0 0 0 0 0 0 0 | 68 | 0 0 0 0 0 0 0 0 0 |
| 33 | 0 0 0 0 0 0 0 0 0 | 69 | 0 0 0 0 0 0 0 0 0 |
| 34 | 0 0 0 0 0 0 0 0 0 | 70 | 0 0 0 0 0 0 0 0 0 |
| 35 | 0 0 0 0 0 0 0 0 0 |  |  |

FIG. 11

EQUATION FOR ELLIPSE:

Unrotated Ellipse-- $k^2z^2+x^2 = L^2$

Rotated Ellipse-- $(k^2c^2+s^2)z^2 + 2(k^2-1)sczx + (k^2s^2+c^2)x^2 = L^2$

Where $c = \cos\theta$ ; $s = \sin\theta$ ; and $k$ = Minor Axis / Major Axis = 0.224   ($k^2$ = 0.05)

$\boxed{\text{FIG. 14}}$ $$\frac{L^2}{x^2} = \frac{k^2}{(k^2\cos^2\theta + \sin^2\theta)}$$

$$d(i,n-1;m,n) = \frac{d_c^2 + k^2 d_q^2}{\Delta x^2} \Delta x = \frac{\sin^2\gamma + k^2 \cos^2\gamma}{\sin^2\phi} \Delta x$$

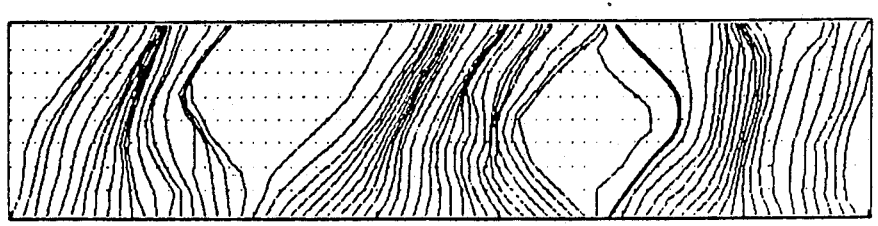
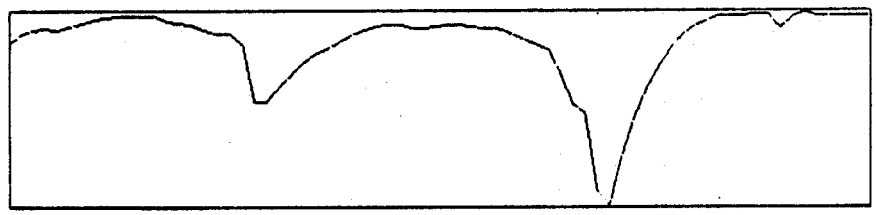
Fig 18
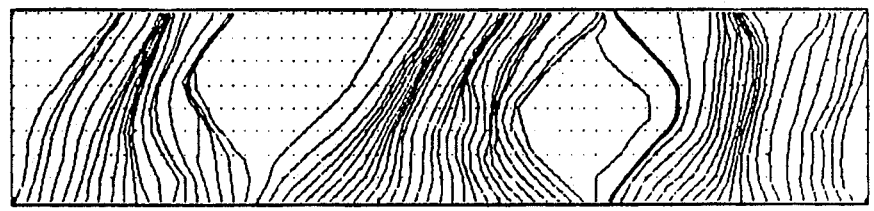
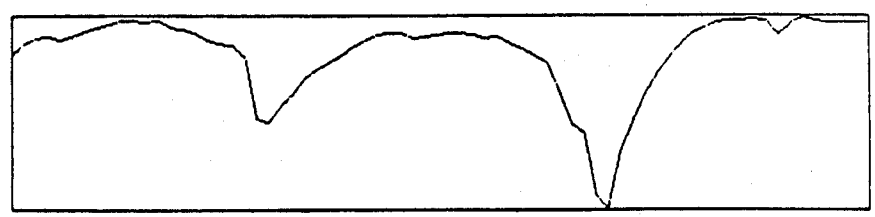
Fig 19

$$D(m,n) = \min_{i}[D(i,n-1) + d(i,n-1;m,n)]$$

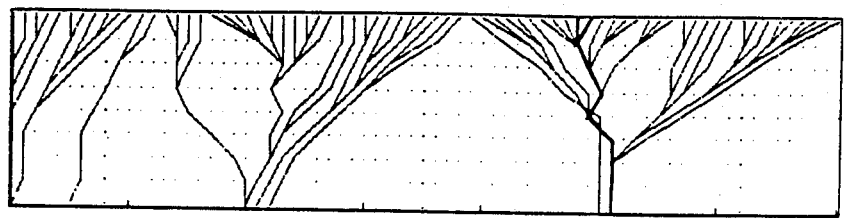
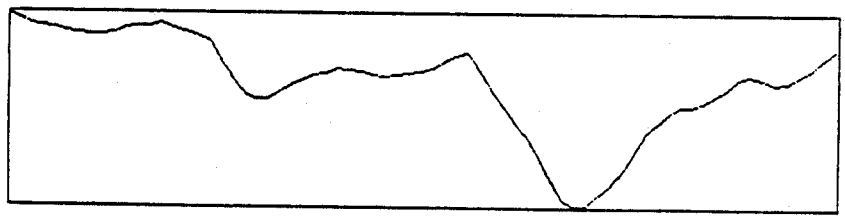
FIG 23
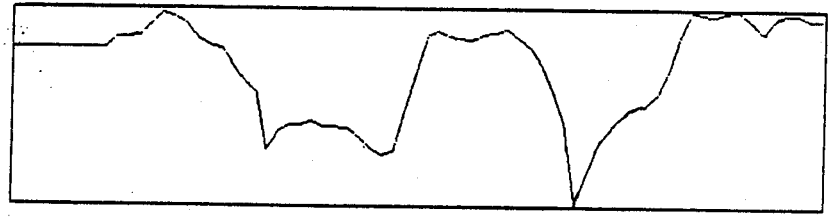
FIG 24

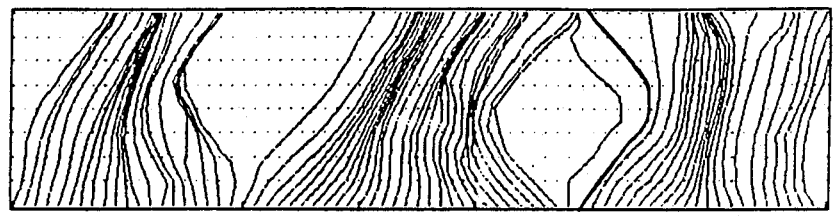
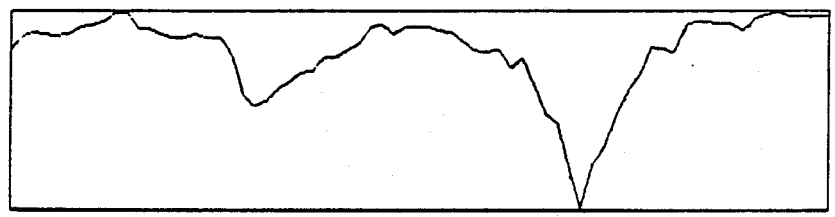
Fig 27
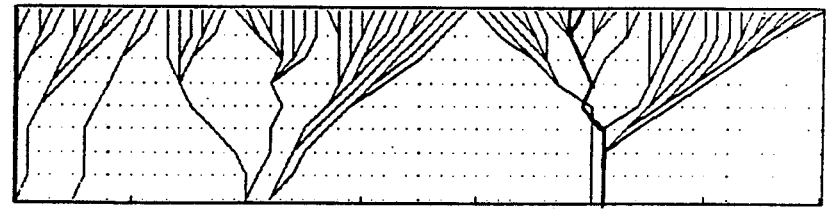
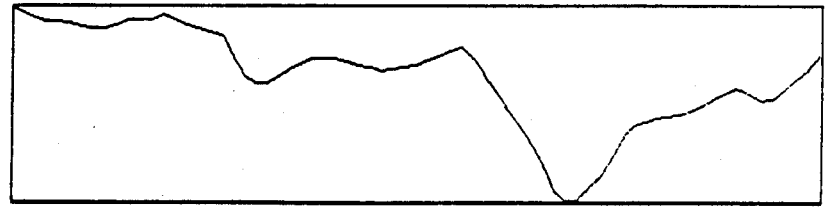
Fig 28

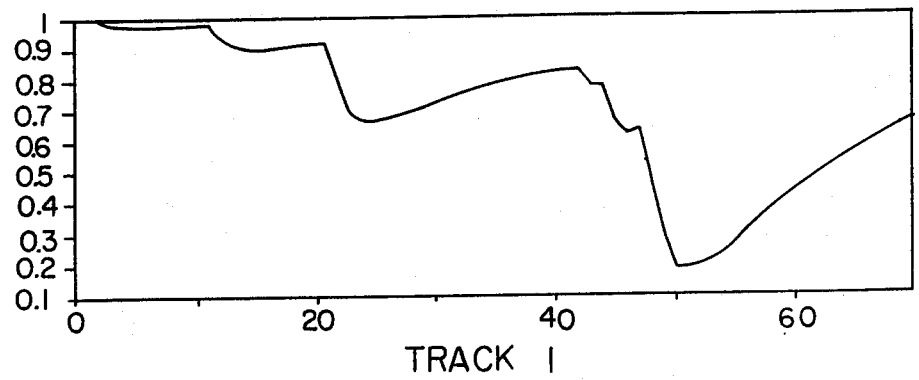
TRACK 1
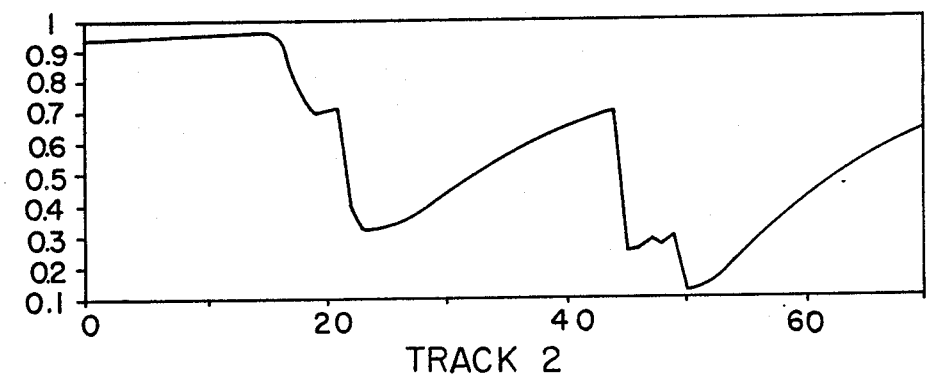
TRACK 2
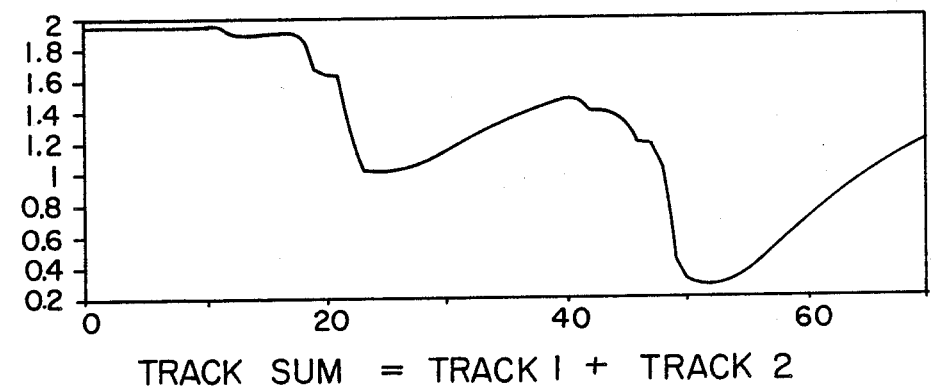
TRACK SUM = TRACK 1 + TRACK 2
Fig 29

NON-DESTRUCTIVE TESTING METHODS FOR LUMBER

TECHNICAL FIELD

This disclosure relates to machine testing and grading of wooden boards by non-destructive methods and equipment.

BACKGROUND OF THE INVENTION

Machine Stress Rating (MSR) is a process by which the stress rating of dimension lumber is determined from a measurement of its stiffness, or Modulus of Elasticity (E). It is known from experimental work that a relationship exists between the bending stiffness of a piece of lumber, and its strength or Modulus of Rupture (MOR). Since the only way to determine MOR is to actually break the piece and measure the load required to break it, the next-best thing in machine stress rating is to measure stiffness, compute modulus of elasticity, and then predict modulus of rupture. Lumber sorted on the basis of E has been found to possess a very good correlation between MOR and grade, as opposed to practically no correlation between visual grade and the breaking strength, or MOR. Load ratings of visually-graded material have been drastically reduced because of the poor correlation between visual defects and the load-bearing capabilities of lumber.

Machine stress rating of dimension lumber has increased the accuracy of lumber grading and hence the efficient utilization of lumber resources. In North America the MSR process involves measuring the flatwise modulus of elasticity (E) of every piece of lumber, automatically spray marking each piece according to its E characteristics, and applying a grade mark according to grade rules. Background information on such testing processes and equipment can be found in U.S. Pat. Nos. 3,194,063 (McKean) and 3,196,672 (Keller).

The machine stress rating program for dimension lumber is now in place in many mills in western Canada, much of the United States, and in other major lumber producing countries of the world. In addition to testing each piece in the production line for flatwise E, a sample of production for each size, species, and grade combination from each shift is tested in edgewise bending for E and strength. In some cases, a tension proof load test is performed also. This off-line quality control program has been designed to assure that the lumber sold as MSR lumber meets the grade requirements for edgewise bending E and strength. In contrast, lumber sold under visual grade rules is not subject to any testing or quality control for structural properties.

Machine stress rating has become a mature concept. Producers know there is a marketplace for MSR lumber if they produce it, and users demanding structural performance know they can depend on a source of supply if they design to the structural values in MSR lumber. MSR lumber has become an attractive component of dimension lumber sales because there are economic incentives for both the producer and the user.

Knowledge of E from the MSR process as practiced today is important in its own right because it determines the deflection of lumber under a given load. It also determines the strength of lumber when it is used as a long thin column. Studies have shown that E can be used as a predictor of lumber bending and tensile strength, and its use in predicting strength accounts for about 50% of the variance of the strength.

A necessary part of the MSR process is to visually inspect each piece of material for defects which are not discernible in the bending stiffness test. It is necessary to down-grade material with excessively large edge-knots, for instance, since these defects have more detrimental effect on edgewise bending strength than is apparent in the flatwise bending measurement of stiffness. The flatwise bending stiffness test remains the best and most practical single method of predicting strength in use; and when the visual overrides are applied, the result is the best method known today to sort material for structural uses.

It is the objective of this disclosure to utilize grain angle measurements in addition to E measurements for lumber grading purposes and for the prediction of lumber strength, specifically the prediction of tensile strength of lumber.

The relationship of strength to grain angle in wood has been stated with a Hankinson formula as:

$$N = PQ/(P \sin^n \theta + Q \cos^n \theta) \qquad (1)$$

where N represents the strength at an angle $\theta$ from the fiber direction, Q is the strength across the grain and P is the strength parallel to the grain. The power n has been found to be in the range 1.5 to 2 and the ratio Q/P in the range of 0.04 to 0.07 for tensile strength.

A Hankinson relation for E has also been found to hold where N, Q, and P are E values at angle $\theta$, across and along the grain respectively. The power n is 2, and Q/P is in the range 0.04 to 0.12. Because the MSR process measures bending E, the prediction of strength depends indirectly on grain angle; consequently, there has been industry skepticism concerning whether direct measurement of grain angle would contribute additionally to strength prediction.

To properly understand the present disclosure, one must look at the distinction between "general grain angle" and "local grain angle" along a wooden board. General grain angle is defined here as the average grain angle over some length of lumber that is long with respect to the extent of knots or other local grain angle perturbations. Excessive general grain angle can be caused by spiral grain in trees, bowed logs, taper, poor sawing or simply the shape of the log before it was cut. Local grain angle is the grain angle defined on a smaller scale, and knots are the usual source of local grain angle problems.

Bending E measurements in production-line MSR equipment must necessarily be over a test span length, typically 900 to 1200 mm, that is long with respect to local grain angle deviations (to avoid significant contributions from compression perpendicular to grain at the lumber-roller interfaces). The effect of poor local grain angle is therefore partially masked by the measurement, which can be shown to be a weighed average of the localized E values along the length of the test span. Thus, it can be inferred that the MSR process accounts for the effect of general grain angle on strength, but does not account for the effect of local grain angle.

The relation between strength and local grain angle is not really conjecture, because experimental work performed over the years in refining the MSR process has shown the importance of visual edge knot determinations (and hence local grain angle) in properly qualifying dimension lumber for the higher MSR lumber grades. The problem, of course, is in being able to visually quantify the sizes and locations of knots and other grain perturbations over the full length of the lumber at production speeds. The fact that the visual graders do function admirably well in this environment is a tribute to their training and attentiveness.

Automated grain angle measurements have been possible since 1977, but the technique has yet to be implemented in the production line. The primary reason for this delay is that no one has demonstrated or presented to the industry a clear vision of how the grain angle data would be used to improve the lumber sorting process.

Details of an apparatus for measuring slope of grain (or grain angle) are disclosed in U.S. Pat. No. 3,805,156 (Norton et al.). The use of such equipment for measurement of geneal grain angle is discussed in an article titled "Measuring General Slope of Grain With the Slope-of-Grain Indicator" (*Forest Products Journal*, Vol. 34, No. 7/8, July/August 1984). Its application to measurement of local grain angle is the subject of an article titled "Measuring Localized Slope of Grain by Electrical Capacitance" (*Forest Products Journal*, Vol. 36, No. 10, October, 1986). The contents of these three publications are hereby incorporated by reference as part of the present disclosure.

Automating the evaluation of local grain angle and its effect on strength relieves the visual grader from having to make this determination, thus freeing the grader for making determinations of other important visual characteristics of the lumber. An automated measurement of grain angle would almost certainly be more accurate than a visual determination and would have the advantage of being the same over time, over different graders, and at different locations. Consequently, a more credible correlation between various types of local grain angle characteristics and lumber strength can be achieved.

"Grain angle," as used in this disclosure, is the direction of the projection of the wood fibers onto the measurement surface. While grain angle is physically measured about a surface of a board, the grain angle values will often be influenced by sub-surface wood grain patterns. The depth of such influence will be dependent upon the specific type of equipment used to measure grain angle, but it is to be understood that surface measurement of grain angle is not necessarily limited to surface wood grain characteristics.

FIG. 1 geometrically illustrates the angular relationship involved in local grain angle measurement. The measurement surface is a plane, which can be either a face F or an edge E of the lumber specimen S, recognizing that the face grain angle $\theta_f$ will usually be different from the edge grain angle $\theta_e$. The zero grain angle reference is taken as a line on the measurement surface parallel to the longitudinal axis of the lumber in the z direction. Positive grain angle is measured counterclockwise from the zero angle reference when looking at the lumber surface from the outside.

One can also define grain angle in three dimensions as a function of both face and edge grain angles so that it is the angle of the wood fibers relative to the longitudinal axis of the lumber. From FIG. 1, which illustrates grain angles $\theta_f$ and $\theta_e$, the grain angle $\theta_a$ as measured from the axis can be stated as:

$$\theta_a = \tan^{-1}(\tan^2\theta_e + \tan^2\theta_f)^{\frac{1}{2}} \quad (2)$$

An excellent approximation for small angles $\theta_e$ and $\theta_f$ is:

$$\theta_a = (\theta_e^2 + \theta_f^2)^{\frac{1}{2}} \quad (3)$$

The earliest commercial grain angle measuring equipment included circuitry for computing $\theta_a$ from the approximate formula. To simplify the present effort, attention shall be limited to the individual projections $\theta_e$ or $\theta_f$. To simplify the notation of measured grain angle, it shall be referred to as $\theta$.

Grain angle measuring equipment of the type described in U.S. Pat. No. 3,805,156 utilizes the fact that the dielectric constant of wood is greater along the direction of the wood fibers than it is across the grain. It applies the concept of rotating capacitor plates at a uniform speed, where the capacitor plates are coplanar sectors of a circle with gaps between them and are arranged so that the wood becomes part of the dielectric medium. A radio frequency field is introduced to the capacitor plates; and a sinusoidal signal is created as the capacitor plates rotate, because the capacitance changes as the field is alternately directed along and then across the fibers. Phase measurement of the sinusoidal signal relative to a fixed reference signal yields a number which can be scaled and translated to obtain the grain angle. In present equipment, measurements are taken at the power-line frequency rate, i.e. at 50 or 60 measurements/second where each measurement is the average grain angle over the lumber area covered by the detector unit capacitor plates during the measurement interval.

Research efforts with grain angle measurements have concentrated primarily on general grain angle determinations. However, the capability of the measuring equipment to determine local grain angle has always been present, and its sensitivity to grain angle perturbations about knots has been known from the first. Existing publications that compare local grain angle measurements from a grain angle indicator with the actual grain angle on a closely spaced grid defined on the surface of a piece of lumber have clearly demonstrated the ability of existing equipment to measure local grain angle.

Several modifications and additions have improved the existing grain angle indicator. Recently, a computer controlled lumber transport mechanism has been developed which has allowed the instrument to be more useful in a laboratory environment. The transport mechanism holds the lumber and, by means of a cable chain attached to the lumber, uses a stepper motor to successively drive the lumber longitudinally over the grain angle indicator detector unit. After each pass of the lumber, another stepper motor causes the detector unit to more incrementally in the transverse direction of the lumber. While the lumber is moving longitudinally, the computer automatically reads and stores grain angle data. When the system has completely scanned the designated surface area of the lumber, the stored grain angle data can be viewed as an array of numbers, each representing the grain angle at a point on a grid previously defined by the operator.

BRIEF DESCRIPTION OF THE DRAWINGS

The preferred embodiments of the invention are illustrated in the accompanying drawings, in which:

FIG. 11 is a visual classification of elementary regions for specimen A;

FIG. 18 shows plots of potential failure paths and a plot of failure distance versus path starting point for specimen A;

FIG. 19 shows plots similar to those in FIG. 18, but illustrates the effect of a failure distance weighting $(L/x)^2$;

FIG. 23 shows plots similar to those in FIG. 21, with a grain angle threshold $\theta_t=25°$;

FIG. 27 shows plots similar to those in FIG. 22, after application of the position dependent weighting function of FIG. 25;

FIG. 28 shows plots similar to those in FIG. 23, after application of the position dependent weighting function of FIG. 25;

FIG. 29 shows cumulative plots of failure distance and combined failure distances for the track model;

FIG. 30 shows a scatter plot of tensile failure stress versus E;

FIG. 31 shows a scatter plot of tensile failure stress versus failure distance using the tracks model;

DETAILED DESCRIPTION OF THE PREFERRED EMBODIMENT

The following disclosure of the invention is submitted in compliance with the constitutional purpose of the Patent Laws "to promote the progress of science and useful arts" (Article 1, Section 8).

NON-DESTRUCTIVE TESTING APPARATUS

Figure 2:
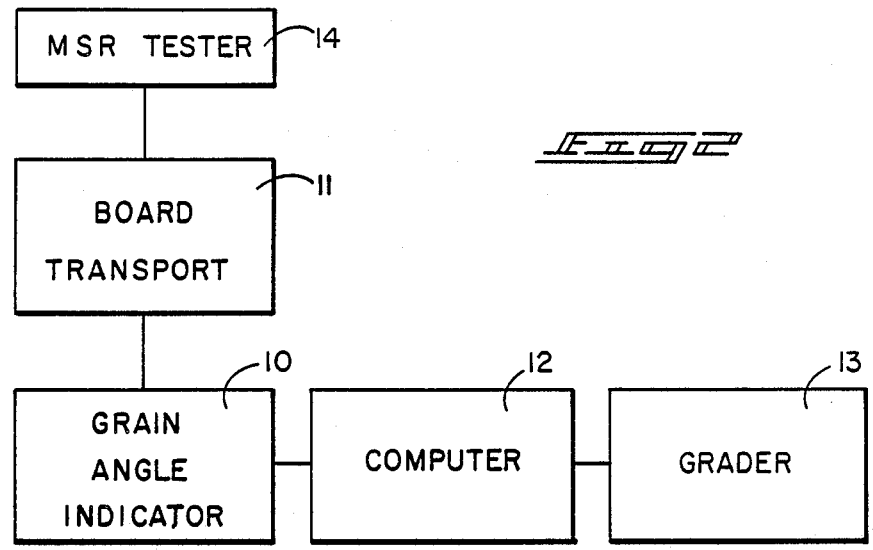
FIG. 2 is a block diagram of the present apparatus.

The apparatus used with regard to the present system is shown in block diagram form in FIG. 2. The grain angle indicator 10 is exemplified by the 510 Slope-of-Grain Indicator available from Metriguard, Inc., of Pullman, Wash., U.S.A., which is based upon the measurement technology disclosed in U.S. Pat. No. 3,805,156. Other types of scanning systems, such as electronic, microwave, optical, photographic, sonic, or holographic equipment can be substituted where the available technology has capability to measure wood grain angle. As shown, each board is moved past the grain angle indicator by a suitable board transport 11. The details of transport 11 are not material to this disclosure so long as it provides relative movement between each board and the grain angle indicator 10 as the board is being scanned. This can be accomplished by movement of the board or by movement of all or part of the grain angle indicator 10. For purposes of illustration, board transport 11 might be a conveyor interposed between an available MSR tester 14 and the grain angle indicator 10 for directing individual boards through both pieces of equipment in a continuous pass. An example of an MSR tester 14 suitable for use in such applications is the Metriguard CLT-Continuous Lumber Tester available also from Metriguard, Inc.

The apparatus is completed by a programmed computer 12 for transforming the grain angle values measured with respect to each board to extract features indicative of knot identification, grain angle perturbations or strength of the board and by a grader 13 for physically processing the individual bords as a function of the extracted features. Computer 12 is preferably a digital electronic computer, but might be operated on optical principles or other techniques, and can be either digital or analog.

Grader 13 can take any physical form applicable to the board processing steps desired at a specific installation. It might mark or physically sort the boards, or it might cut out specific sections of the boards as a function of the extracted features.

NON-DESTRUCTIVE TESTING METHOD

The method described below for non-destructively testing wooden boards involves the initial step of measuring local grain angle values in a geometric pattern about each board, the transformation of grain angle values measured with respect to each board to extract features indicative of knot identification, grain angle perturbations or strength of the board, and the step of physically processing the individual boards as a function of the extracted features. The method is applicable to simplified grading or sorting procedures where boards are processed after merely identifying the presence of knots, as well as to more sophisticated strength estimation procedures usable in conjunction with the present lumber strength testing processes.

The transformation of grain angle features can involve the determination of curl or divergence values, which are vector functions of measured grain angle values. Both permit physical identification of knot location and size. A combination of curl and divergence, termed gradient, as well as data transformations termed edges and knots yield more distinctive results. Finally, knot identification can be achieved by various pattern matching techniques. The application of these techniques to lumber grading applications and processing of lumber is beyond the state of present utilization of measured grain angle values.

Strength estimation for tested boards involves transformations of grain angle values to determine failure distance, which is a function of tensile strength for lumber. Failure distance can be determined by various computational techniques, including an ellipsoidal model, a search model, and a track model.

SAMPLING GRAIN ANGLE VALUES

Grain angle can be considered as a real valued function defined at each point of the measurement surface. Ideally the grain angle indicator 10 would sample the grain angle at each of the measurement grid points. If the grid mesh about the board is fine enough, the Sampling Theorem allows the signal to be reconstructed from the samples. Simply stated, if the grain angle signal is sampled at intervals more closely spaced than one half the period of the highest spatial frequency present in the signal, then it is theoretically possible to recover the original signal from the samples. In the present system, the highest frequencies occur near knots, whose edges correspond to very high spatial frequencies. To reduce the sampling requirement, the data can be smoothed or filtered to remove the signal's high frequency content. Smoothing reduces the sharpness of the edge definition, but it allows sampling on a coarser grid. If sampling occurs on a grid coarser than allowed by the Sampling Theorem, then a phenomenon known as aliasing occurs, whereby high frequencies can masquerade as other frequencies.

Sampling by the presently available wood grain angle indicator is not ideal, in that measurements are not made at theoretical points on the measurement surface. Deviations from ideal sampling occur because the capacitor array covers an area of the measurement surface larger than a point, and because it reads deeper than the surface. Also the wood typically is moving with respect to the capacitor array and finally, the signal is electronically filtered by the instrument.

The capacitor array diameter D of the grain angle indicator 10 controls the surface area averaged into each measurement when the lumber is stationary with respect to the capacitor array location.

The grain angle measurement, as well as averaging over the area under the capacitor array, also averages from the lumber surface into the lumber. This does not affect the result where uniformity is assumed in the depth direction, but it does in the general case. The depth of reading into the wood decreases as the gap between the plates decreases. Also, the data from material near the surface is more heavily weighted than data from the interior material.

Because each grain angle measurement is not instantaneous, there is a smoothing of the grain angle data presented to the sensitive capacitor plate array during the measurement interval. The exact nature of this time weighting function is unknown but a reasonable assumption is that its shape is exponential with time constant approximately equal to one period of the ac power line frequency.

Additional smoothing is performed by filters in the electronic system. Their purpose is to reduce noise in the system and not to reduce aliasing.

Several options are available to reduce aliasing of the data. The size of the capacitor plate array can be increased so that its diameter is larger than twice the distance between samples; the lumber speed can be increased so that it is greater than twice the distance between samples divided by the measurement time constant estimated here as one period of the ac power line frequency; or the distance between samples can be decreased.

The first two options reduce the spatial resolution of the measurement. The third option of decreasing distance between samples will improve resolution until the distance is less than ½ the capacitor plate array diameter or until it is less than ½ the lumber speed multiplied by the measurement time constant. Further reductions in distance between samples will have a lesser effect on the resolution.

FEATURE EXTRACTION

The most important task in the development of pattern recognition or estimation techniques is the initial reduction of data to a manageable amount so that automated methods can be effectively utilized. If grain angle data are sampled at points spaced closely enough that the underlying grain angle function can be obtained from the sample data, then sampling causes no loss of information. The challenge is to reduce this quantity of data so that knots can be identified, or strength estimated.

Techniques for data reduction are called feature extraction. Stated another way, feature extraction is the process of throwing out as much as possible of the data without throwing away significant information that would affect the classification or estimation process. After the feature extraction step, knot identification or strength estimation is possible with automated methods.

To help with the effort of feature extraction, one must investigate various methods of viewing grain angle data efficiently.

The development of this disclosure began with samples of grain angle and investigation of data processing methods that allow knot identification and strength estimation features to be chosen. Plots of the data and transformations of the data that were considered are the grain angle field, contours of constant grain angle, contours parallel to grain, contours perpendicular to grain, contours of curl, contours of divergence, edge contours, and knot contours.

Figure 1:
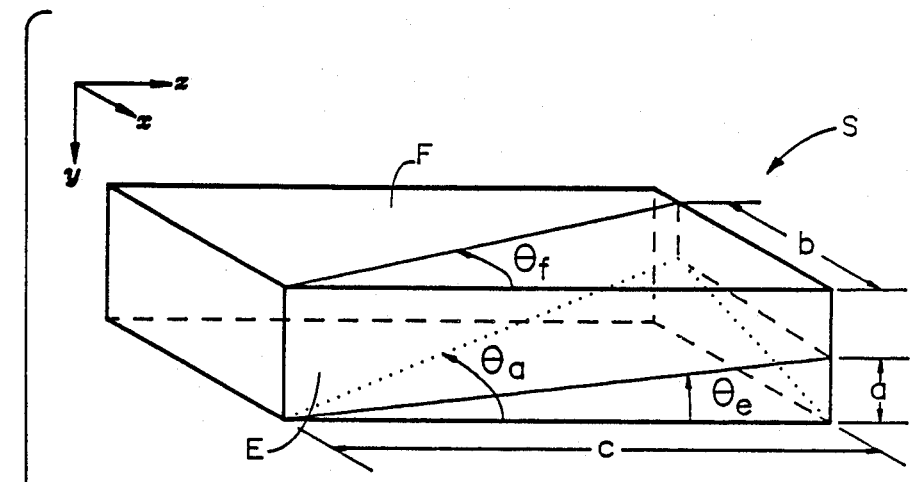
FIG. 1 is a three dimensional geometric view of the angular relationships present in a tested board.

The spatial coordinate system used in this disclosure is shown in FIG. 1. Coordinate z is along the major axis of the piece of lumber, x is across the face and y is down the edge. For the present discussion the analysis has been simplified to two dimensions and uniformity is assumed in the y direction. It will be evident that the model can be extended into three dimensions to include variations in the y direction. The concepts can be presented and discussed more easily in two dimensions. For testing, the lumber initially selected was substantially uniform in the y direction.

Figure 3:
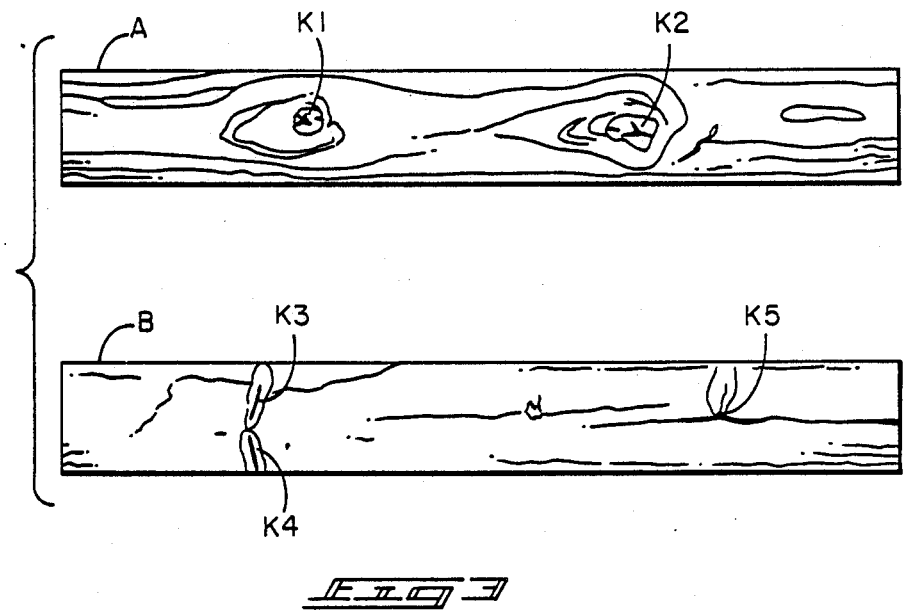
FIG. 3 illustrates scanned surface characteristics of two board specimens.

Grain angle measurements were taken at each point of a two-dimensional 8 cm×70 cm grid array, 1 cm apart in both the z and x directions on two boards A and B shown in FIG. 3. The sampled angle at a general point in the grid is labeled $\theta(m,n)$, where m and n ($0 \leq m \leq M$, $0 \leq n \leq N$) are integers defining location in the z and x directions, respectively. For present purposes, the largest values the subscripts take on are $M=8$ and $N=70$.

To illustrate each of the methods used to look at the data, plots are presented in FIGS. 4–10 and 13 corresponding to the two pieces of 2×4 lumber shown in FIG. 3. The first specimen of lumber A had two clearly visible tight knots K1 and K2 extending through it. The second specimen B had spike knots K3, K4 and K5 extending from the edges into the wide face. Although both faces and both edges of the 2×4 lumber pieces were tested, the FIGS. 4–10 and 13 utilize measurements from one face only. The spike knot example in specimen B is included here for illustrative purposes; it clearly violates the assumption of uniformity in the y direction.

Figure 4:
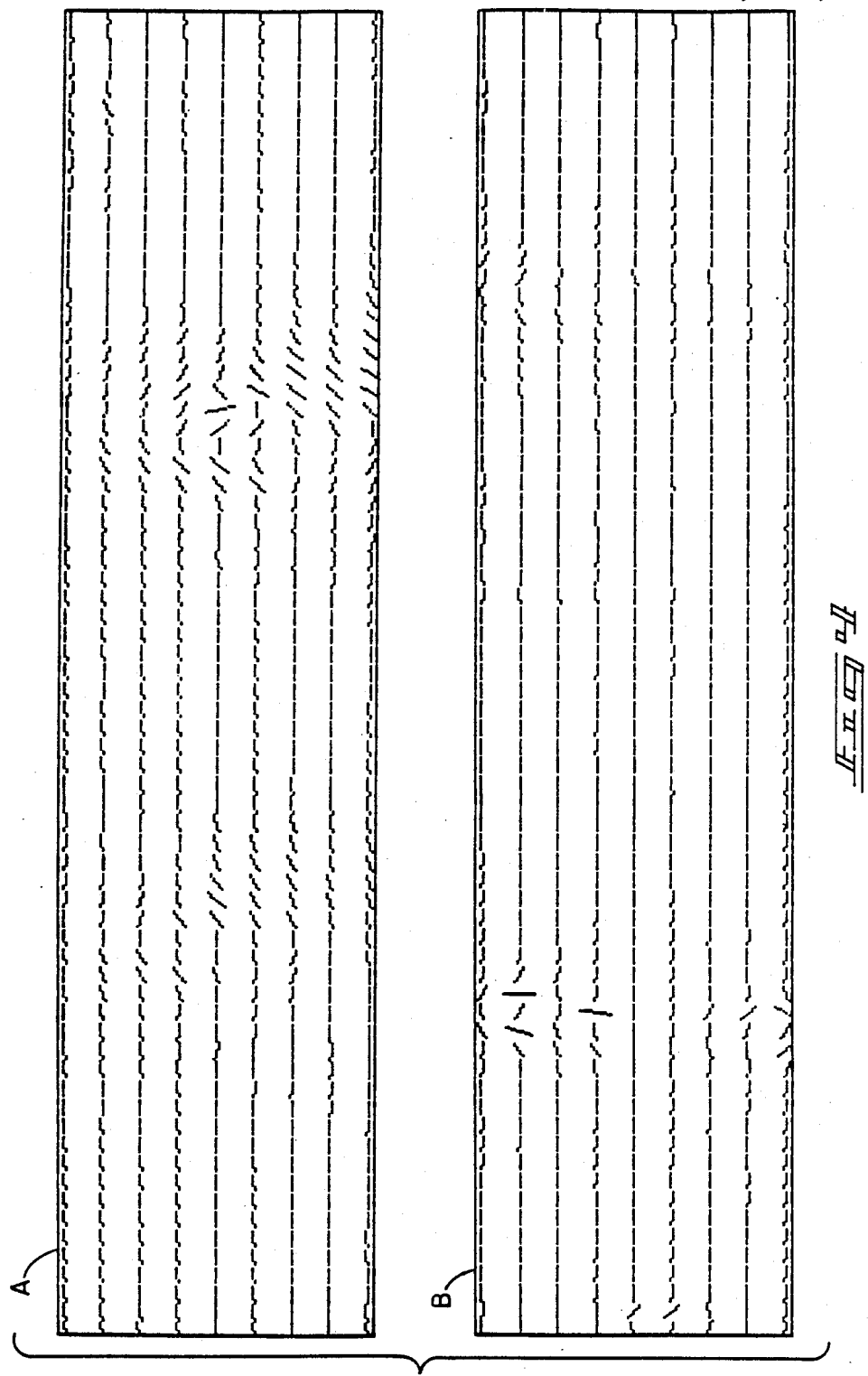
FIG. 4 shows grain angle fields for the specimens of FIG. 3.

If a line segment is plotted representing the grain angle at each point on the sampling grid, the result will appear as in FIG. 4. Each line segment is located at a sampling point and is oriented at an angle equal to the measured angle at that point. The lengths of the line segments are identical. If the line segments are though of as vectors, they define a vector field which will be called the "grain angle field".

The grain angle field is currently defined in two dimensions. The third component and the variation of the first two components in the third direction are assumed to be zero. In general, this is not true, and a full three-dimensional model should be used.

Figure 5:
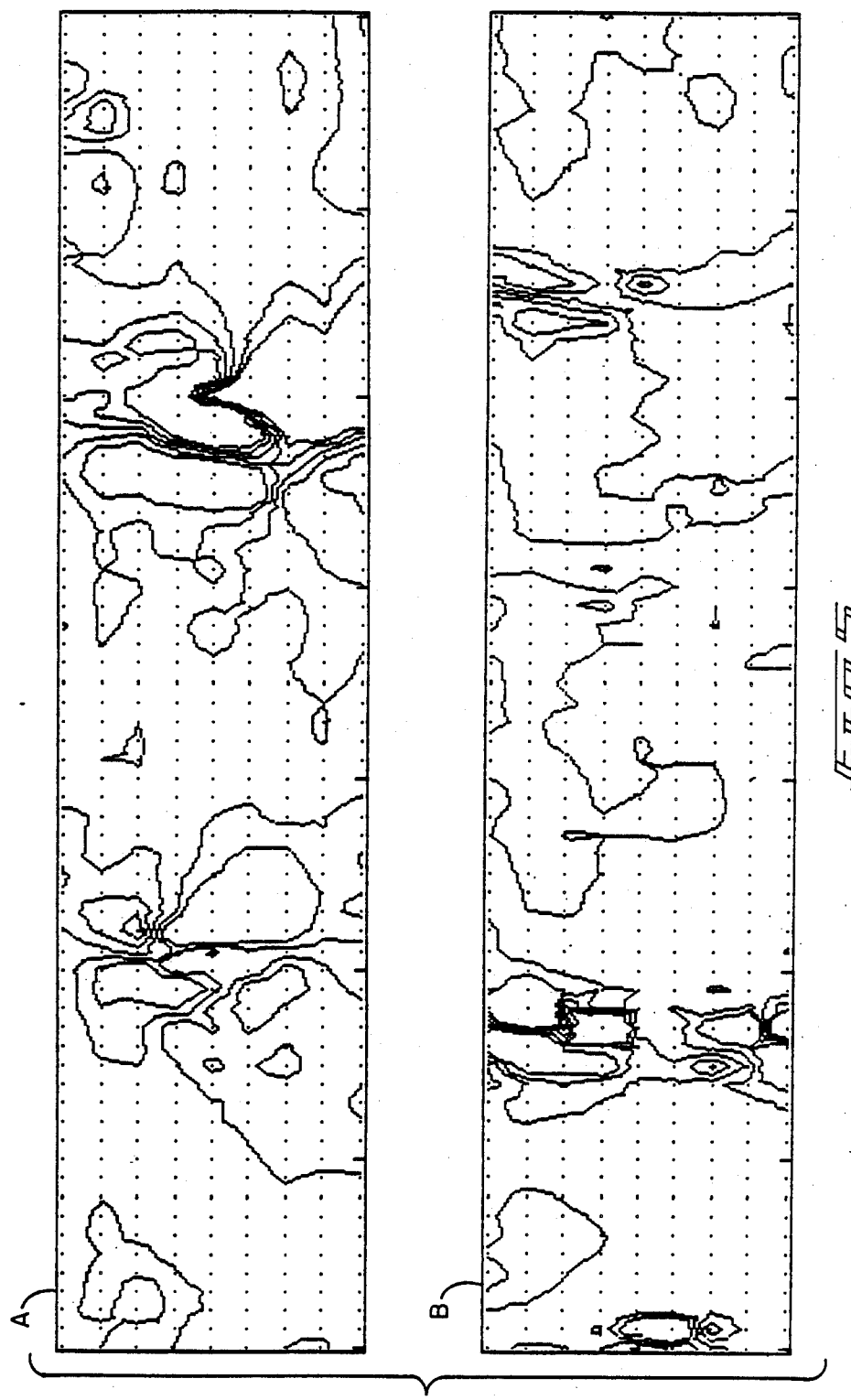
FIG. 5 is a plot of the contours of constant grain angle for the specimens of FIG. 3.

FIG. 5 shows contours of constant grain angle for the lumber specimens A and B. Diagonally opposite areas of high and low grain angle about the knots of specimen A can be observed.

Figure 6:
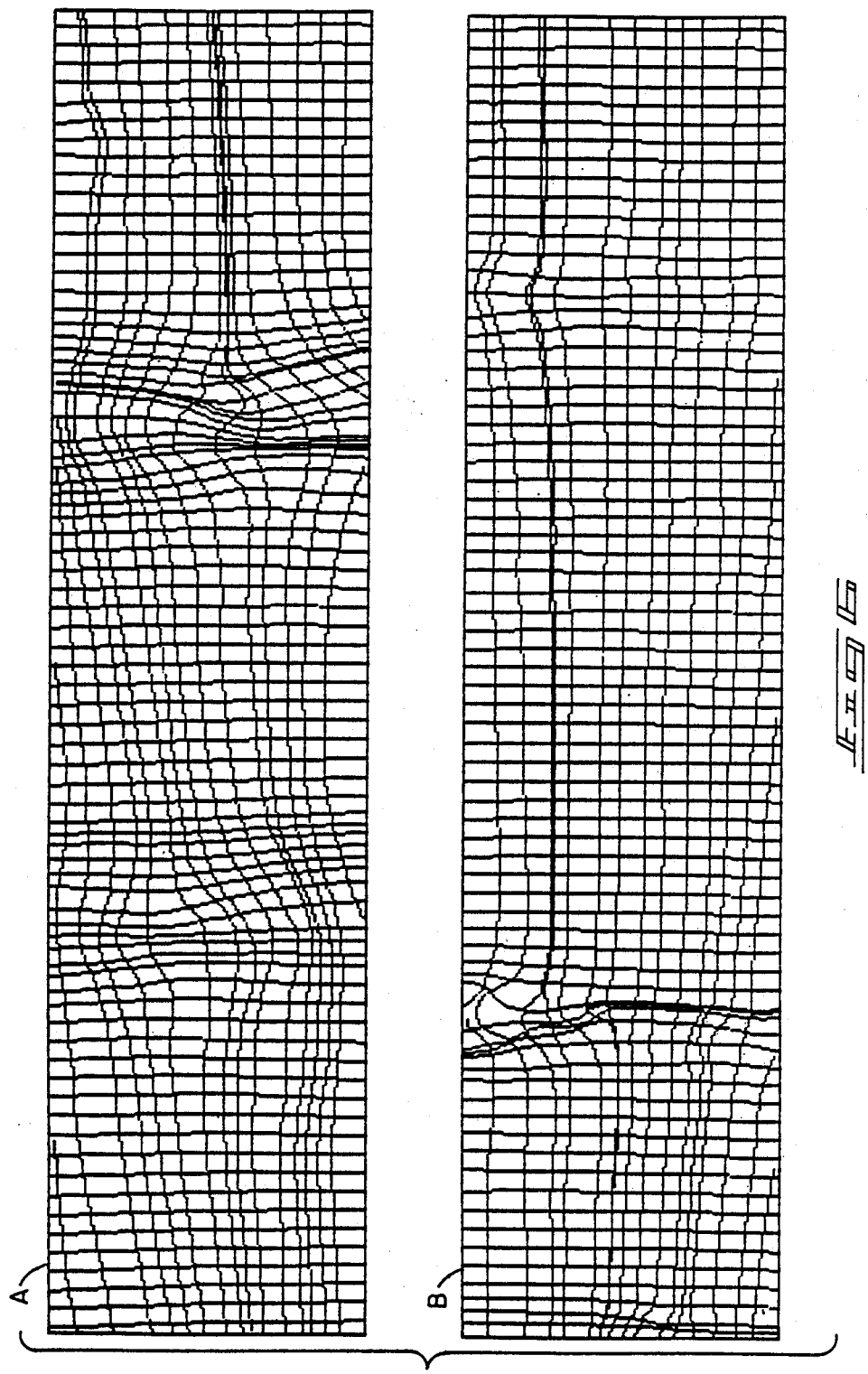
FIG. 6 is a plot of grain lines and lines orthogonal to the grain lines for the specimens shown in FIG. 3.

FIG. 6 illustrates the grain lines obtained by joining line segments head to tail in the measured direction at each line segment. These lines correspond to the direction of the wood fibers. Also illustrated on FIG. 6 are contours orthogonal to the grain direction. The aspect ratio of these and other computer generated plots is not 1:1, hence the lines do not appear to be orthogonal everywhere on FIG. 6. The plotted aspect ratio 2:1 can be seen from FIG. 5, which illustrates the 1 cm×1 cm sampling grid points.

KNOT IDENTIFICATION BY CURL

Figure 7:
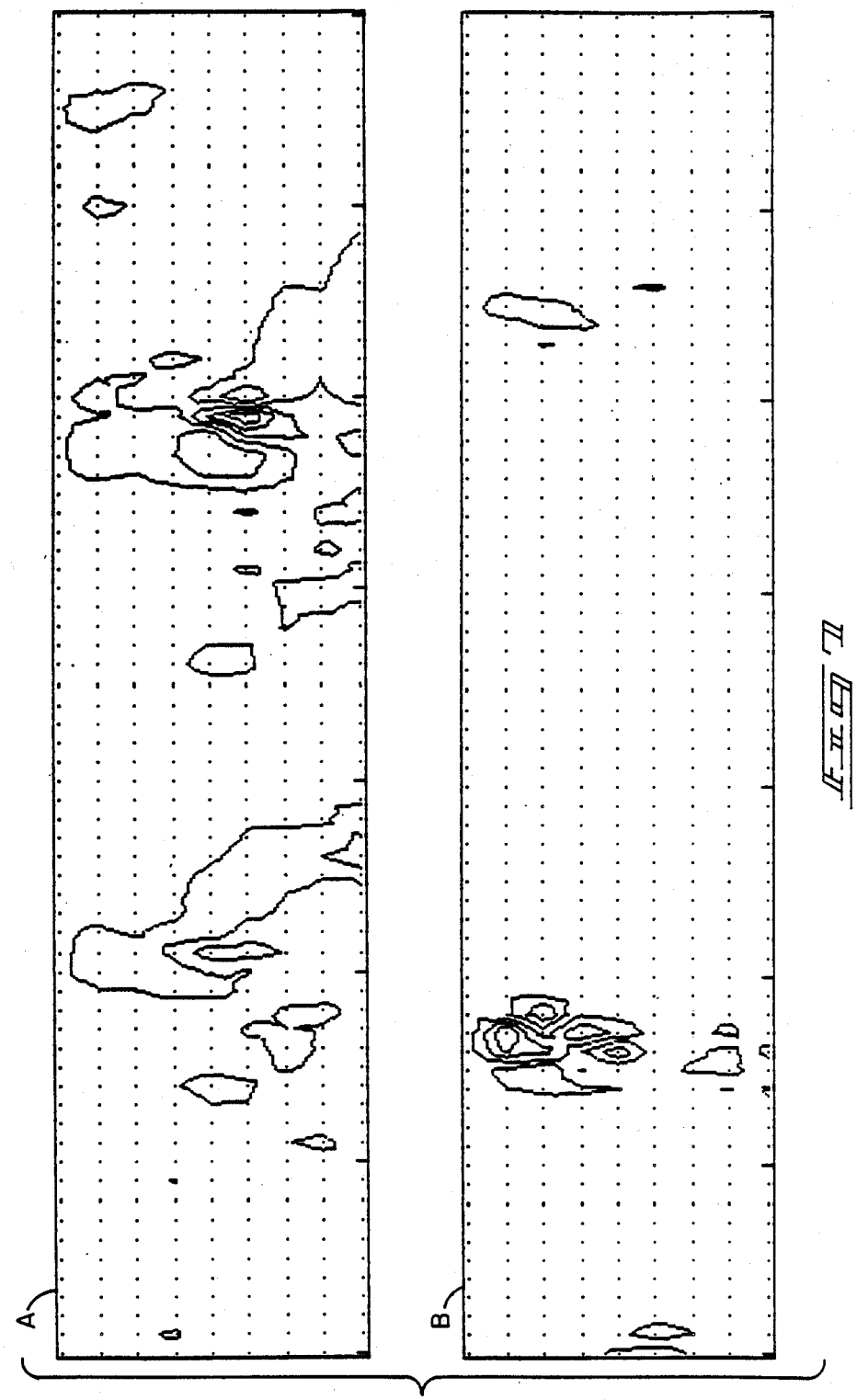
FIG. 7 is a plot of the contours of constant curl for the specimens shown in FIG. 3.
Figure 8:
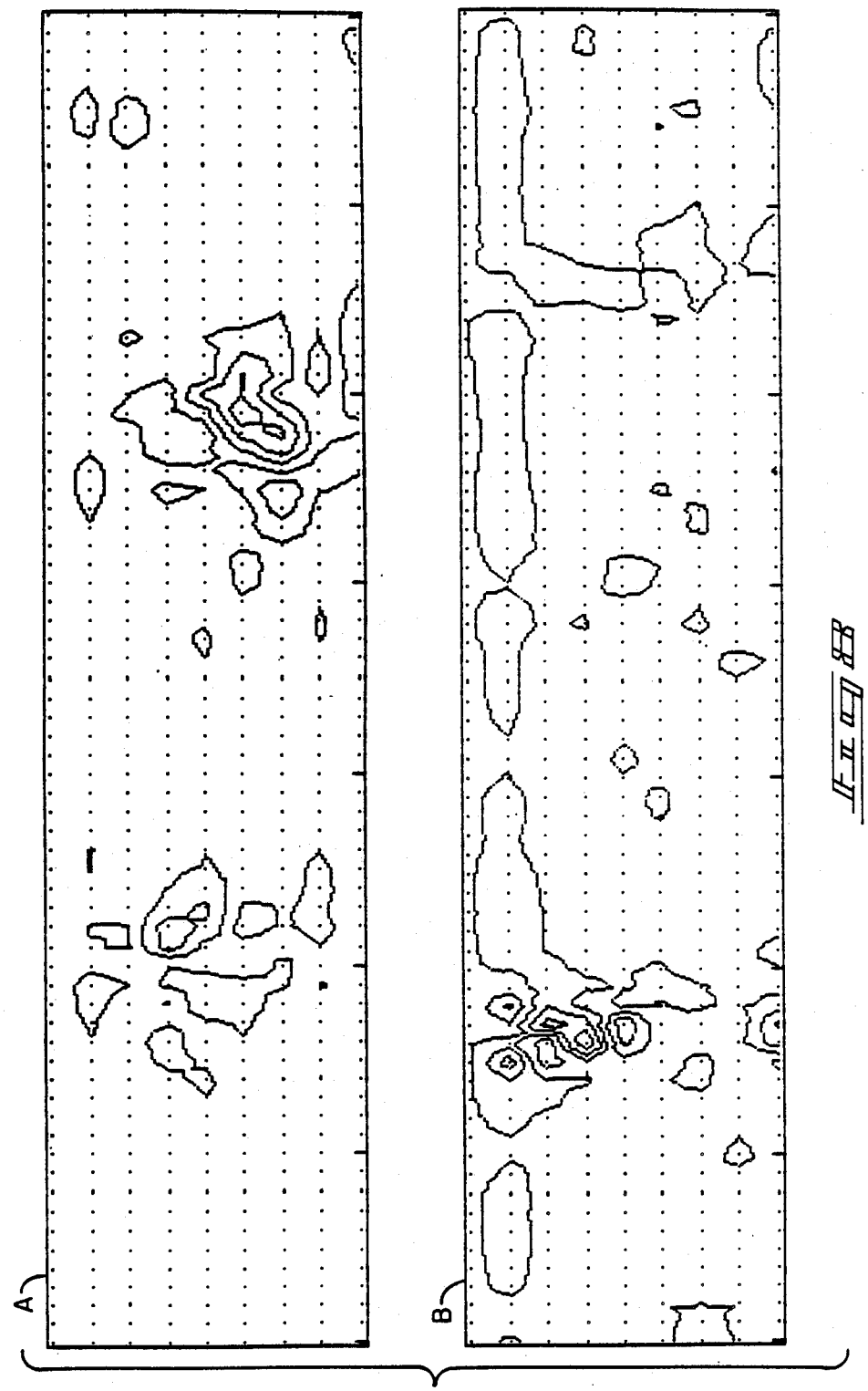
FIG. 8 is a plot of the contours of constant divergence for the specimens shown in FIG. 3.

In vector calculus, a differential quantity known as "curl" is defined for vector fields. Curl is a point property of the field that describes how an infinitesimal body would rotate in the field if the field were a fluid with fluid velocity corresponding to strength and direction of the field. If the wood had uniform grain aligned in some direction, then the curl is an indicator of deviations from uniform grain. FIG. 7 illustrates contours of constant curl for the lumber specimens A and B. Curl is a vector quantity; however, in the present two-dimensional case, curl is aligned with the third axis. Consequently, the scalar plot of FIG. 7 showing constant contours of the third component of curl is a complete representation of curl. It can be seen that the computational transformation of grain angle values to curl yields data representative of the knot and grain patterns visually evident in specimens A and B.

KNOT IDENTIFICATION BY DIVERGENCE

Another differential vector field property is "divergence". Divergence is a point property of the field describing sources or sinks of fluid from or into the point—again using a fluid analogy. If the wood had uniform grain aligned in some direction, then the divergence of the grain angle field would be zero. Thus, divergence is also an indicator of deviations from uniform grain. Divergence is a scalar quantity, and contours of constant divergence are plotted in FIG. 8 for the specimens A and B. Again, a direct relation of divergence to the scanned surface characteristics of specimens A and B is evident.

KNOT IDENTIFICATION BY EDGES

Figure 9:
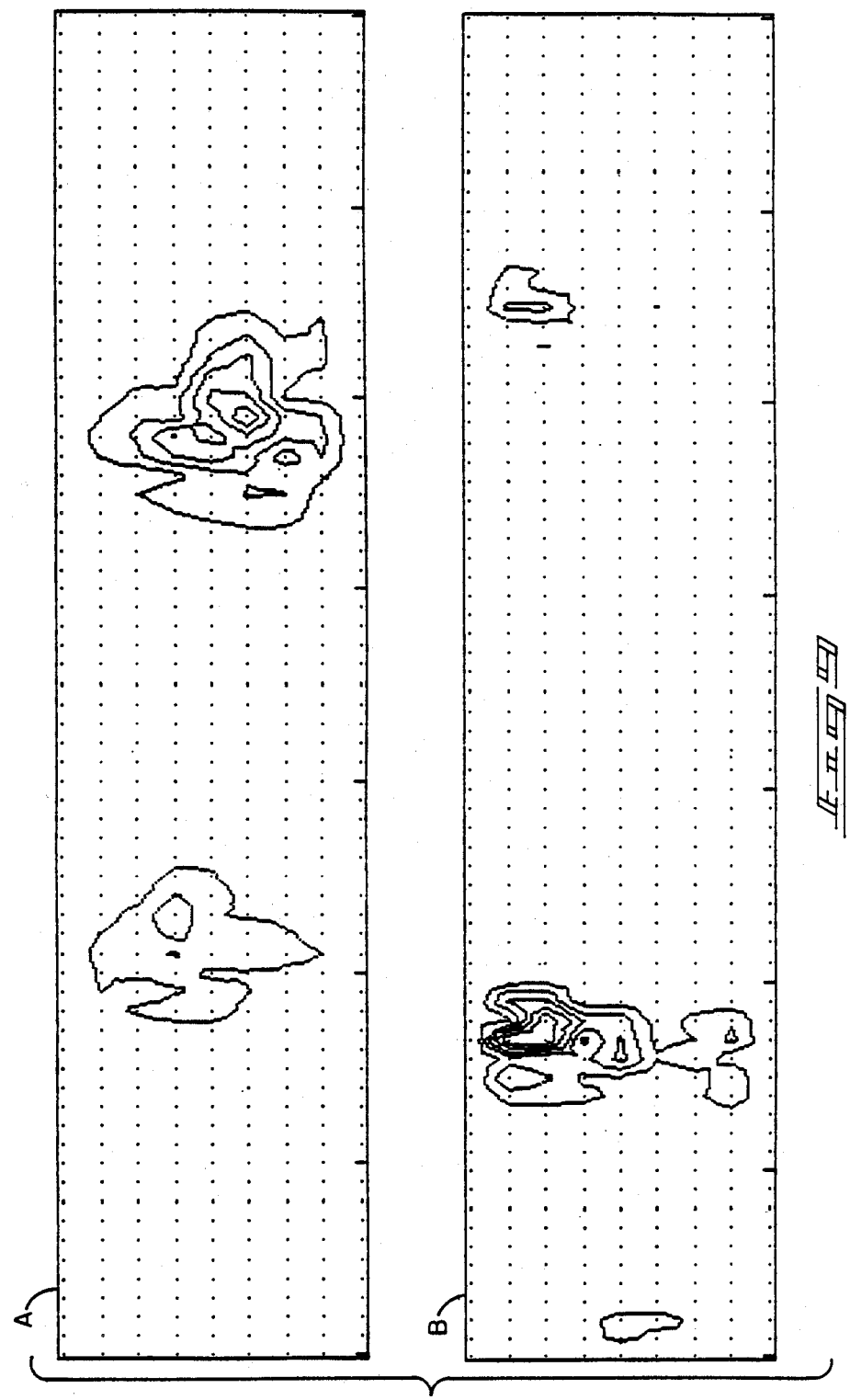
FIG. 9 is a plot of the contours of constant value for the edges transformation for the specimens shown in FIG. 3.

A data transformation called "edges" was devised that looks for change in the data. One can think of the edges transformation as sorting out the areas of high spatial frequency. FIG. 9 illustrates contours of constant value for the edges transformation for the specimens A and B. Knot location and size is very clear.

KNOT IDENTIFICATION BY KNOTS

Figure 10:
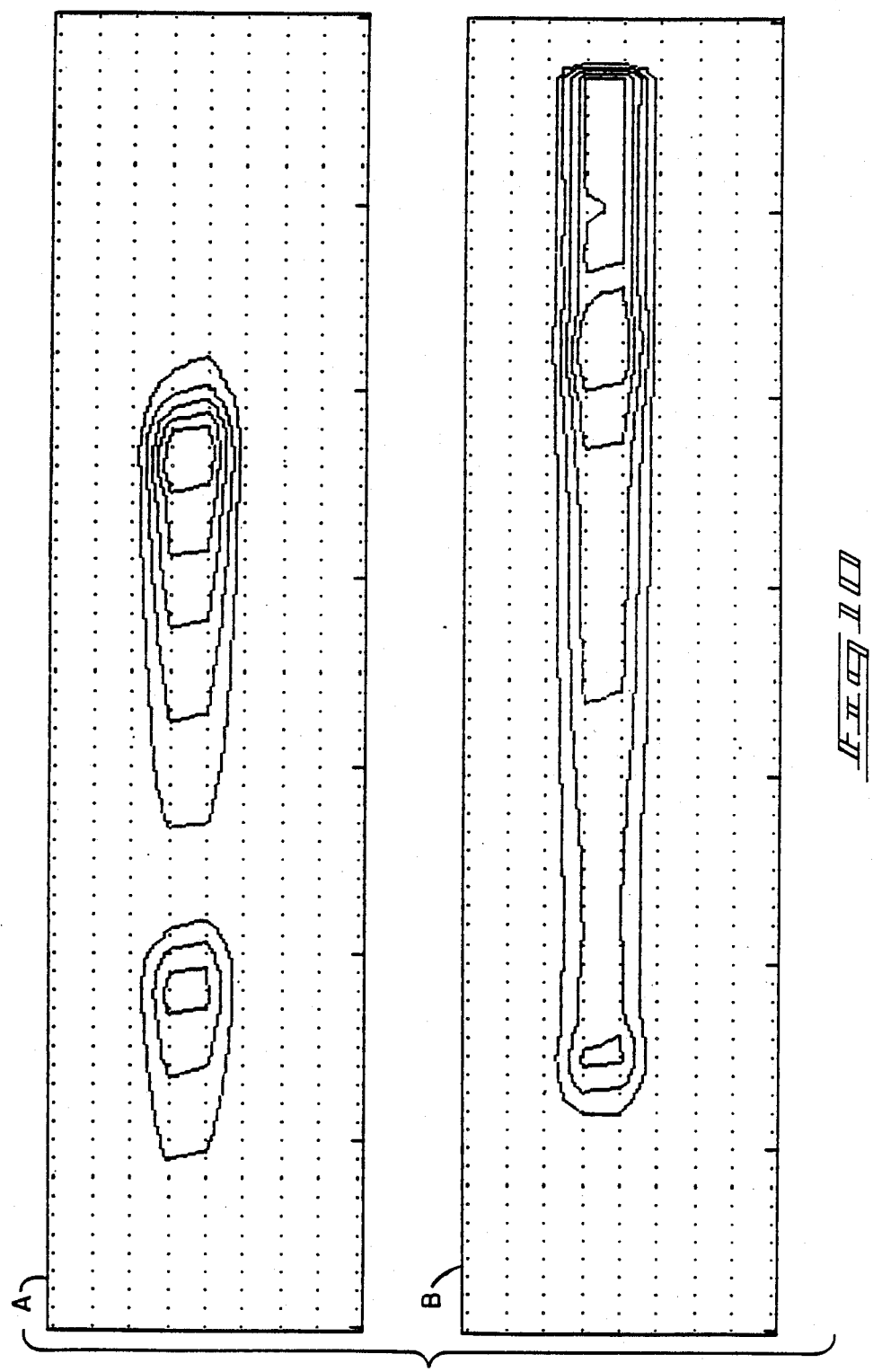
FIG. 10 is a plot of the contours of constant value for the knots transformation for the specimens shown in FIG. 3.

A data transformation called "knots" was designed after observing from the contours of grain angle (FIG. 5) that for a location centered about a knot, the grain angle in the neighborhood of the knot is positive in the second and fourth quadrants but negative in the first and third quadrants. FIG. 10 illustrates the results of applying the knots transformation to data taken from the specimens A and B.

KNOT IDENTIFICATION BY GRADIENT

Figure 12:
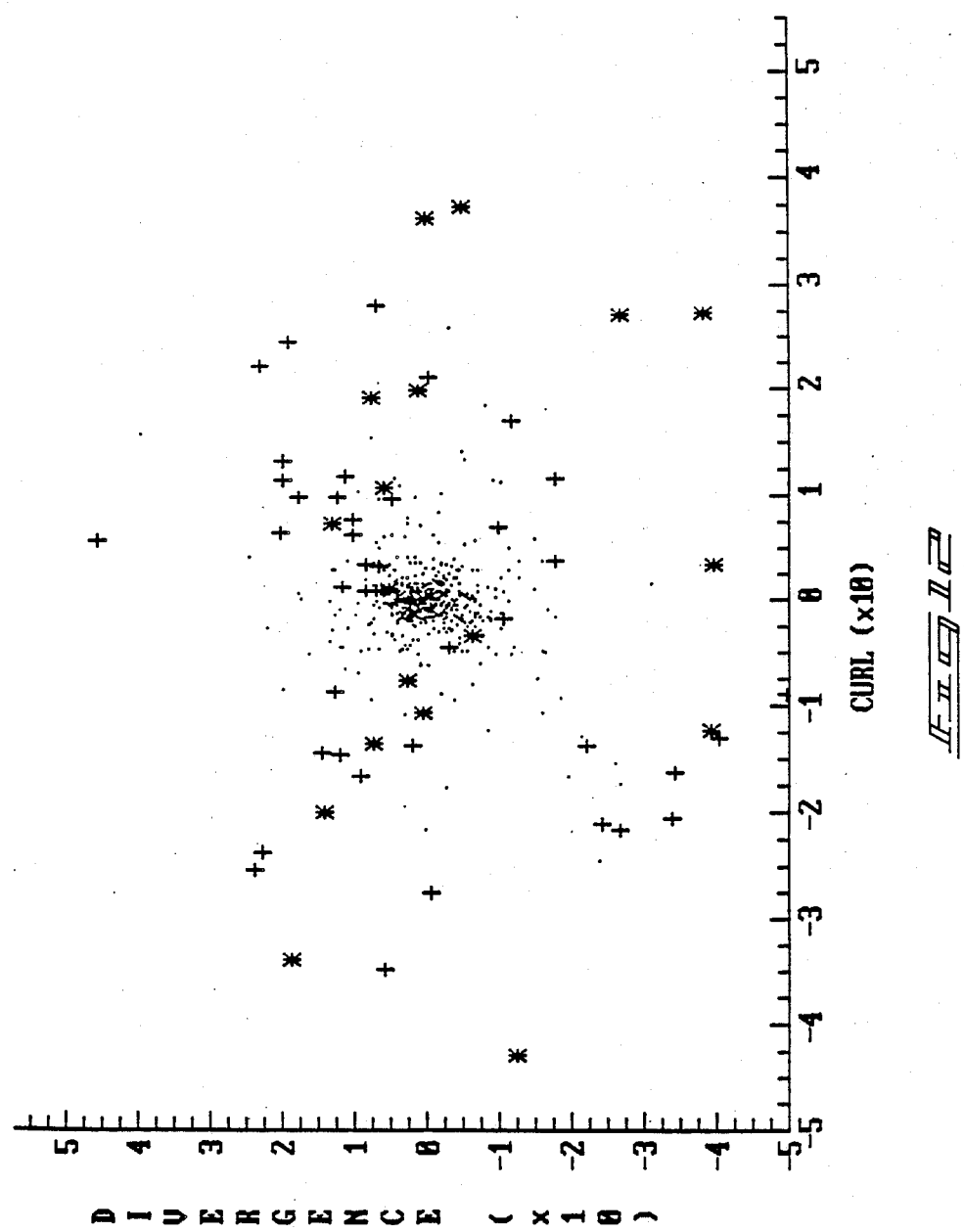
FIG. 12 is a plot of divergence and curl for specimen A, with uniform grain being shown by dots, transition areas being shown by plus signs, and knots being shown by asterisks.
Figure 13:
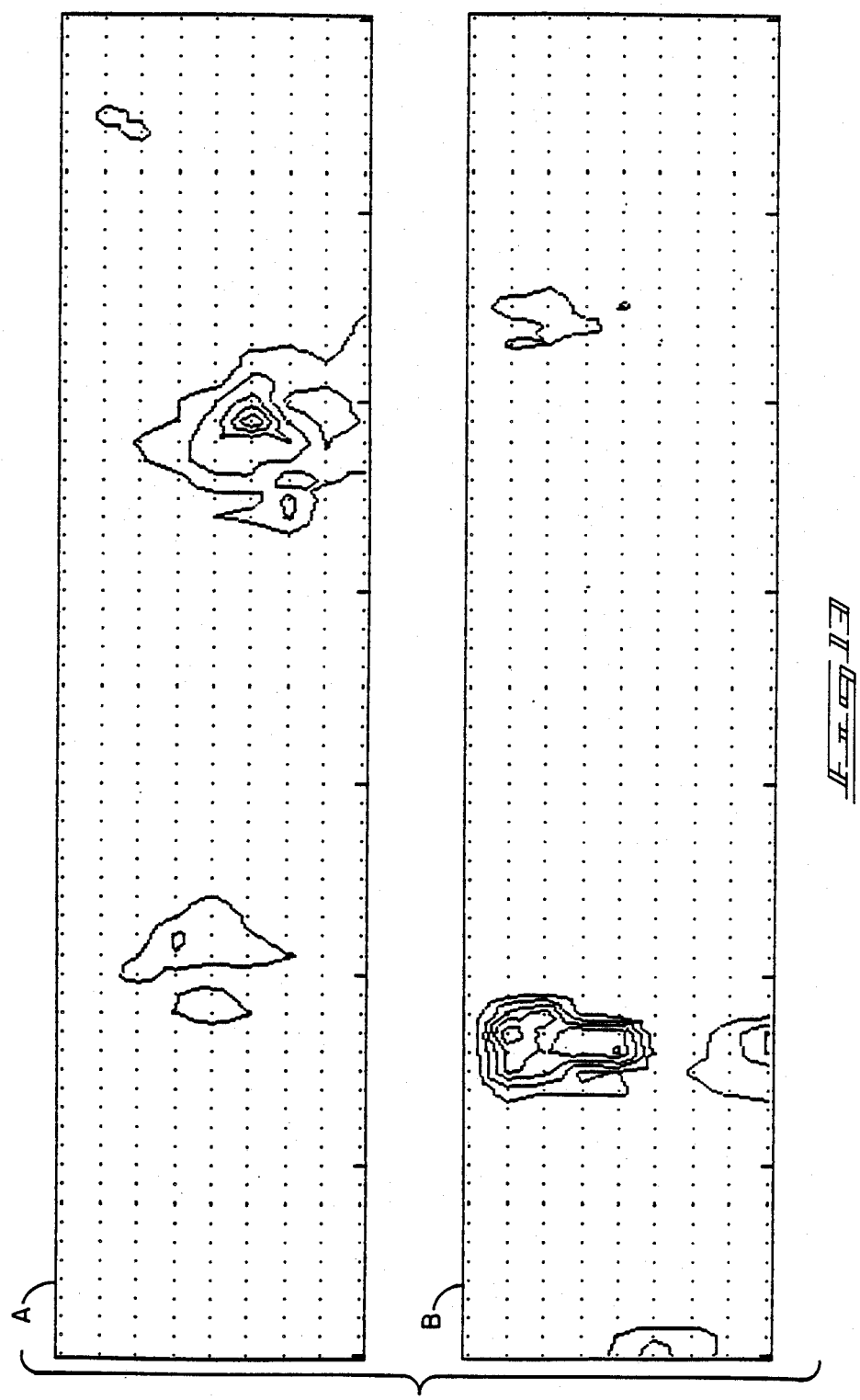
FIG. 13 is a plot of the contours of equal gradient magnitude for the specimens shown in FIG. 3.

Following initial testing, it was surmised that some combination of curl and divergence would show up the knots. To test this idea, the elementary regions of the measured face of Specimen A were visually classified into three zones: uniform grain, transition, and knot, labeled by numerals 0, 1 and 2, respectively, on the grid presented in FIG. 11. Then a point for each elementary region was plotted in a two-dimensional space where curl is the abscissa and divergence is the ordinate. The result (FIG. 12) shows that the uniform grain regions (shown as dots) were clustered near the origin of zero curl and divergence. The regions identified as containing knots (shown as asterisks) were scattered in the plane away from the origin. This suggests using a measure for knot identification consisting of the distance "r"

(or $r^2$) away from the origin in the curl-divergence plane. Evidently, $$r = (|curl|^2 + divergence^2)^{\frac{1}{2}}$$

For the two-dimensional case, the distance r is equal to the magnitude of the gradient of grain angle $\theta$. Implementation of this transformation, which is defined as "gradient" leads to the plot of FIG. 13, where contours of equal r are shown.

KNOT IDENTIFICATION BY PATTERN MATCHING

In addition to the above specialized functions, the transformation of grain angle values by computer 12 can apply the Cauchy-Schwarz inequality to the measured grain angle values and a preselected stored pattern at a plurality of locations on the scanned board surface. Based upon the previously-described observation of grain angle patterns about a knot location, the stored pattern can be expressed as a matching function applied to the measured grain angle values to identify a location having grain angle values of the same sign in diagonally opposed quadrants about the location and further having grain angle values of opposite signs in adjacent quadrants about the location.

LUMBER GRADING APPLICATIONS

For lumber grading purposes, knot locations are obtained as the locations of the maxima of the knots, edges or gradient functions and the size of a knot can be taken as the area over which the appropriate function exceeds some threshold. The results of the above transformations applied to measured grain angle data from lumber with knots provide definite indications of the location and size of knots. For example, results in FIGS. 9 and 10 for the edges and knots transformations clearly show up the knots that are present in specimens A and B. To a lesser degree, the results in FIGS. 7 and 8 for curl and divergence also indicate the presence of these knots.

The extracted features resulting from the above transformations can effectively serve as components of an automated lumber grading system. In a very simple application, identification of knot locations might be used to sort clear grain lumber from lumber containing knots. When used in conjunction with Machine Stress Rating equipment, the extracted features can be processed within computer 12 to downgrade the stress rated lumber based upon predetermined levels that take into account factors such as knot size, frequency and/or location on each tested board.

STRENGTH ESTIMATION

Estimating the strength of lumber in the past has meant categorizing it according to its measured E value and then downrating it according to the severity of visual characteristics including grain angle. The concept of "strength ratio" has been introduced to cover this. This disclosure approaches tensile strength estimation by taking into account the effects of local grain angle. Three models for strength estimation have been developed, and the resulting estimated strength values were compared with measured strength for a sample of 24 pieces. The strength estimation models utilize the concept of "failure distance" which is defined in the following paragraph.

Failure distance is the distance which, if multiplied by the clear wood ultimate tensile failure stress parallel-to-grain, would give the tensile strength of the piece. Failure distance has units of length for this work because the underlying disclosure herein uses a two-dimensional model, thereby assuming uniformity in the third direction. If a full three-dimensional model were used, then failure distance would become failure area. For example, consider testing a 2×4 board, which has a width of 3.5" (89 mm). Suppose the clear wood failure stress parallel to grain is 8000 psi (55 MPa) which, when multiplied by thickness to accommodate the two-dimensional model, becomes 12000 pounds/inch (2090 N/mm). Then, if the 2×4 has clear straight grain, it would be assigned a failure distance of 3.5" (89 mm), giving a failure strength of (3.5 inch) (b 12000 pounds/inch)=42000 pounds ((89 mm) (2090 N/mm)=187 KN). In the case where the lumber does not consist of clear straight-grained wood, the failure distance would be evaluated by the chosen strength estimation model to be less than the geometric distance. Then, multiplication of this lesser failure distance by the ultimate tensile stress for clear wood would yield a failure strength less than the value for clear wood.

The following discussion shall use the earlier description of a rectangular coordinate system for the wood, with z being the distance measured along the wood axis, x being measured across the face, and y being the dimension across the edge (see FIG. 1).

ELLIPSOIDAL MODEL

The ellipsoidal model used to develop failure distance for strength estimation according to this disclosure is based upon the following equation for an ellipse:

$$X'R'ARX = L^2 \qquad (11)$$

where $$X = \begin{bmatrix} z \\ x \end{bmatrix}$$

is a two-dimensional vector in the (z,x) plane, $$A = \begin{bmatrix} k^2 & 0 \\ 0 & 1 \end{bmatrix}$$

is a 2×2 matrix with $k^2$ a real constant less than 1, $$R = \begin{bmatrix} \cos\theta & \sin\theta \\ -\sin\theta & \cos\theta \end{bmatrix} = \begin{bmatrix} c & s \\ -s & c \end{bmatrix}$$

is a 2×2 rotation matrix of angle $\theta$, L is a positive real scalar, and ' indicates matrix transpose. Carrying out the indicated matrix multiplication yields:

$$R'AR = \begin{bmatrix} k^2c^2 + s^2 & k^2sc - sc \\ k^2sc - sc & k^2s^2 + c^2 \end{bmatrix} \qquad (12)$$

Figure 14:
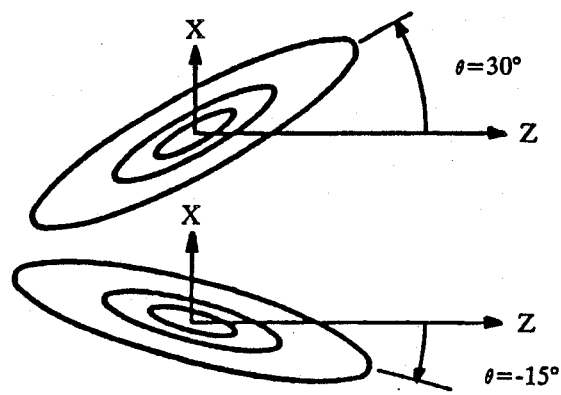
FIG. 14 illustrates basic ellipsoidal geometry.

FIG. 14 is a plot showing ellipses in the (z,x) plane for different values of L and rotation angle $\theta$. The constant $k^2$ for these ellipses was chosen to be 0.05. The value k=0.224 is the ratio of minor to major axis length.

Figure 15:
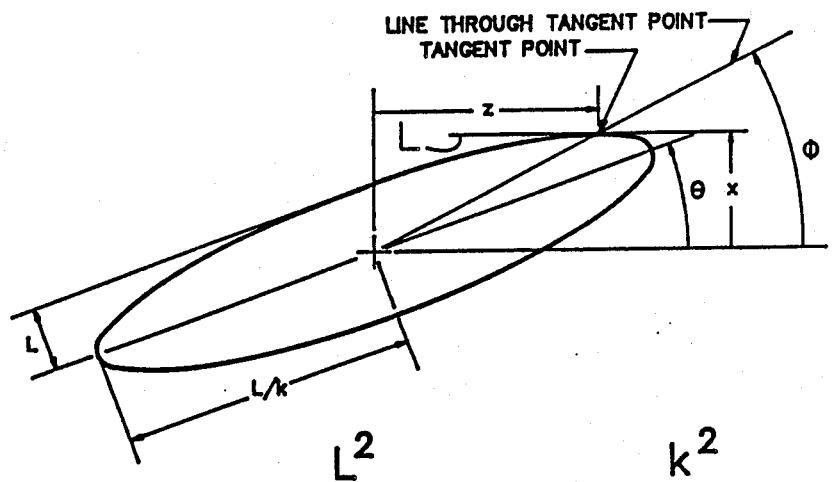
FIG. 15 illustrates geometric relationships between an ellipse and horizontal tangents, where the ellipse is the smallest ellipse at angle $\theta$ which reaches the value x in the (zx) plane.

One additional piece of geometry is needed before defining the ellipsoidal model. Let a horizontal (x=constant) line L be drawn tangent to an ellipse as shown in FIG. 15. The condition for horizontal tangency is that the gradient of the scalar function $L^2 = X'RARX$ points in the x direction, or:

$$[\text{Gradient } X'R'ARX]' \begin{bmatrix} 1 \\ 0 \end{bmatrix} = 0 \qquad (13)$$

It is known that $$\text{Gradient } X'R'ARX = 2R'ARX \qquad (14)$$

Hence Equation (13) becomes:

$$(k^2c^2+s^2)z+(k^2-1)scx=0 \qquad (15)$$

Therefore the point of tangency must fall on the line:

$$x=bz \qquad (16)$$

where the slope b is obtained from Equation (15) as:

$$b=(k^2c^2+s^2)/((1-k^2)sc) \qquad (17)$$

Also, because the point of tangency (z,x) is on the ellipse, we have from Equations (11) and (12).

$$(k^2c^2+s^2)z^2+2(k^2-1)sczx+(k^2s^2+c^2)x^2=L^2 \qquad (18)$$

Substituting for z in terms of x from Equations (16) and (17), and simplifying yields:

$$L^2/x^2 = k^2/(k^2c^2+s^2) \qquad (19)$$

Figure 16:
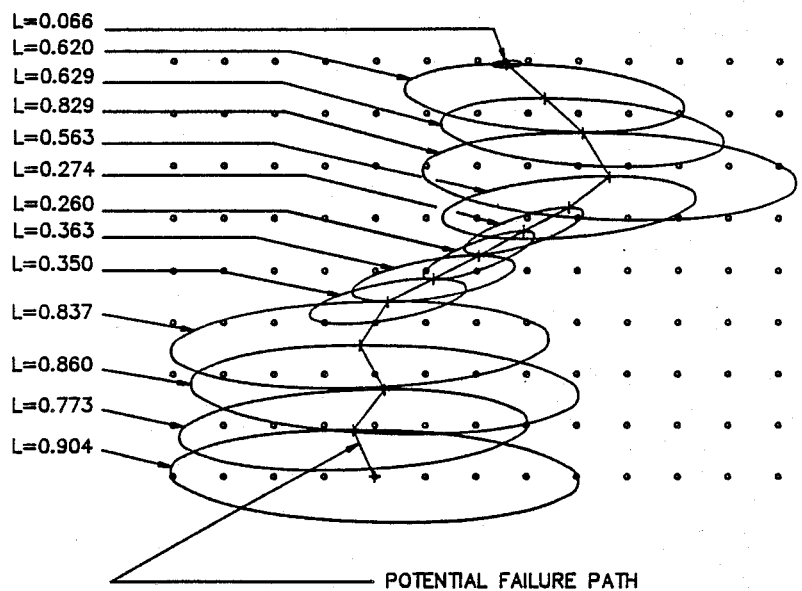
FIG. 16 illustrates the ellipsoidal development of the failure path in relation to measured grain angle. Each ellipse is drawn centered at the end of the previous path increment and oriented at measured angle $\theta$. The size of the ellipse is controlled by the path increment length and the measured grain angle. The largest ellipse occurs when $\theta=0$ and the smallest when $\theta=90°$.

In describing the ellipsoidal model, it is necessary to first define a family of potential failure paths each starting at a grid point along one edge of the lumber and ending sat the other edge. Then, for each path a failure distance is computed as the sum of incremental failure distances for segments along the path. FIG. 16 illustrates a set of ellipses defined by this procedure. Finally, the failure path is chosen as the one giving minimum failure distance, and the strength estimate is proportional to this minimum failure distance.

A particular potential failure path is defined for the first segment as a vector $\bar{r}$ of length r starting at a particular edge grid point and aligned in the direction that minimizes the ratio of failure distance increment divided by the x component of $\bar{r}$.

Each failure distance increment is defined as the value L (see Equation (18)) for an ellipse that is oriented with grain angle $\theta$, centered at the starting point of vector $\bar{r}$ and passing through the end point of vector $\bar{r}$. From FIG. 15, it can be seen that the ratio L/x is minimized for vector $\bar{r}$ chosen at angle $\phi$ to the lumber axis where $$\phi = \tan^{-1} b \qquad (20)$$

and b is the slope defined in Equation (17). Vector length r is chosen to be small enough so that the measured grain angle $\theta$ does not vary much over its length. Now the x component of $\bar{r}$ is given by:

$$x = r \sin \theta \qquad (21)$$

From Equations (19) and (21), the value L is computed as $$L = (k^2/(k^2c^2+s^2))^{\frac{1}{2}} r \sin \theta \qquad (22)$$

This value of L used in Equation (18) defines an ellipse tangent to the horizontal line having the constant x value given by Equation (21).

The ellipsoidal model assumes that the failure path includes the vector $\bar{r}$ and increments the failure distance by amount L. If another vector of length r is started from the end of the first and the same procedure is followed, both the failure path and failure distance can be incremented. This procedure is then repeated until the failure path reaches the other edge of the lumber. The length of the last failure path segment is adjusted so that the board edge is just reached. The result is a failure path and a failure distance evaluated starting at a specified point on one edge of the lumber. The same procedure is repeated along the length of the board, beginning from each edge point on a grid along one side of the lumber. Each path so defined is a potential failure path. The failure path for a board can then be estimated as being at the location of the one giving the smallest failure distance. The smallest failure distance multiplied by the ultimate tensile failure stress parallel to grain is the strength estimate. FIG. 18 illustrates potential failure paths and a plot of failure distance from each edge point for the lumber specimen A. The heavy line shows the path yielding the smallest failure distance.

The ratio $(L/x)^2$ of Equation (19) is a result that looks much like Hankinson's Formula, Equation (1). In fact, if we divide Equation (1) by P and then the numerator and denominator of the right side by P, we obtain:

$$(N/P) = (Q/P)/((Q/P)\cos^n \theta + \sin^n \theta) \qquad (22A)$$

By identifying the ratio Q/P of cross-grain tensile strength to along-grain tensile strength as $k^2$, the ratio N/P of tensile strength at grain angle $\theta$ to along-grain tension strength as $(L/x)^2$, and let n=2 (a value allowed according to published USDA Forest Products Laboratory materials), it can be seen that Equation (19) is Hankinson's Formula. The geometric interpretation is in FIG. 15, where the L and x values can be seen explicitly. This suggests weighting the distance by $(L/x)^2$ instead of (L/x) as was done initially in the ellipsoidal model. Whereas the failure distance increment L originally used was just (L/x)x, it is better to use $(L/x)^2$ as an alternative failure distance increment. FIG. 19 illustrates failure paths and a plot of failure distance from each edge point along one edge for the lumber specimen A by using $(L/x)^2$ weighting. Again, a heavier line shows the path yielding the smallest failure distance.

SEARCH MODEL

A limitation of the ellipsoidal model is that the next failure increment along any potential failure path occurs in the direction of least failure strength. In practice it is known that the failure path sometimes includes more than one knot separated longitudinally along the piece. To accommodate this failure mode, it may be necessary to search and in fact occasionally to increment the failure path along higher strength regions in order to pick up lower strength on the other side. Consequently, a search model for estimating failure strength was developed.

Figure 20:
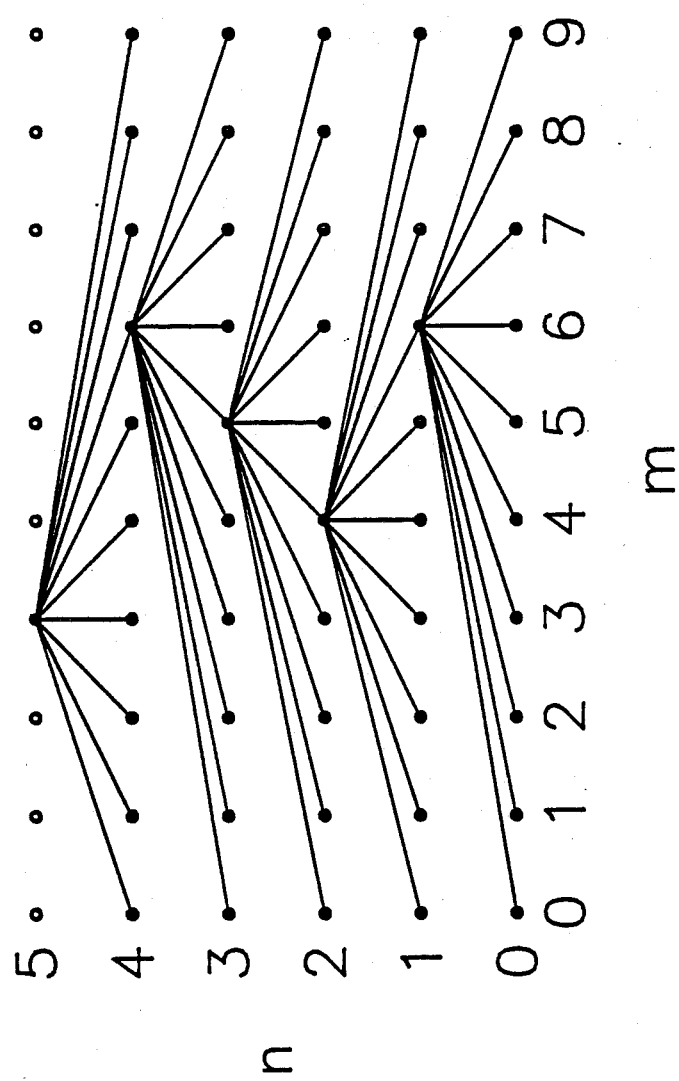
FIG. 20 is a diagram illustrating potential failure paths about a specimen grid.

The search model is based upon the assumption that for tensile failure to occur, the lumber must fail from one edge to the other. It attempts to find the failure path that gives the minimum failure distance across the lumber. FIG. 20 illustrates potential failure path segments in a grid m points long and n points wide. It graphically shows the possible paths in a progression working downwardly from the top of the grid. The search is limited to paths going through the measurement grid points. Each of the grid points along the lumber edge for which n=N is potentially on the failure path. For example, consider the point (m,N). The failure distance $D(m,N)$ associated with the point (m,N) is given by:

$$D(m,N) = \min_{i}[D(i,N-1) + d(i,N-1; m,N)] \quad (23)$$

where $D(i,N-1)$ is the failure distance across the piece to point $(i,N-1)$, and $d(i,N-1;m,N)$ is the failure distance from point $(i,N-1)$ to point $(m,N)$. The search for minimum occurs over all i along the measurement grid track for which n=N−1. The same process is used to define the failure distance to each point (m,N−1) along the adjacent grid track. Similarly the failure distance to the general grid point (m,n) is:

$$D(m,n) = \min_{i}[D(i,n-1) + d(i,n-1; m,n)] \quad (24)$$

for $0 \leq m \leq M, 1 \leq n \leq N$ and $$D(m,0) = 0, \quad 0 \leq m \leq M \quad (25)$$

To reduce processing time requirement, various restrictions can be placed on the extent of the search performed in Equation (24). For example, the index i can be limited to only a certain index count q on each side of the target index m. Then Equation (24) becomes:

$$D(m,n) = \min_{m-g \leq i \leq m+q} [D(i,n-1) + d(i,n-1; m,n)] \quad (26)$$

Figure 17:
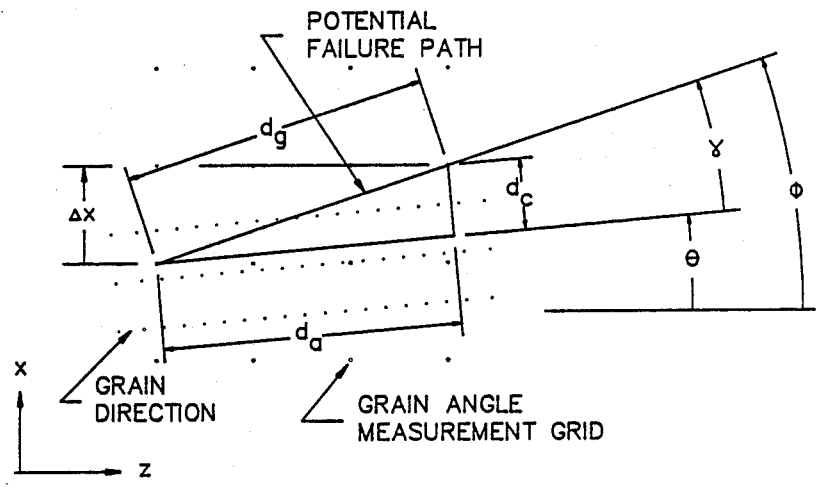
FIG. 17 is a diagram illustrating the decomposition of a potential failure path into component $d_c$ across the grain and $d_a$ along the grain. Angles $\theta$ and $\phi$ are measured from the lumber axis to the direction of the wood fibers and to the potential failure path, respectively.

The remaining challenge was how to define the failure distance increment $d(i,n-1;m,n)$ for the failure path from the grid point $(i,n-1)$ to the grid point $(m,n)$. The path was defined as a straight line between the two points. Because it is more difficult to force a failure to occur across the fibers than along the fibers, the potential failure path was decomposed from $(i,n-1)$ to $(m,n)$ into its components $d_c$ across and $d_a$ along the grain as illustrated in FIG. 17. These components are:

$d_c = d_g \sin \gamma$ $d_a = d_g \cos \gamma$ where $d_g$ is the geometric length of the potential failure path and angle $\gamma$ is:
$\gamma = \phi - \theta$
$\phi$ = angle from lumber axis to the potential failure path.
$\theta$ = angle from lumber axis to the measured grain direction.

To define the failure distance increment, the x component of the potential failure path was weighted with $R^2$, a dimensionless ratio whose numerator is a modified measure of failure path length and whose denominator is the x component $d_x$ of the potential failure path. More specifically, $R^2$ is given by:

$$R^2 = \frac{d_c^2 + k^2 d_a^2}{d_x^2} \quad (27)$$
$$= \frac{d_g^2 \sin^2\gamma + k^2 d_g^2 \cos^2\gamma}{d_g^2 \sin^2\phi}$$
$$= \frac{\sin^2\gamma + k^2 \cos^2\gamma}{\sin^2\phi}$$

where $k^2 \approx 0.05$ is a number less than 1 used to give less credit to the along grain component $d_a$ than the across grain component $d_c$.

Then, the failure distance increment for the potential failure path from (i,n−1) to (m,n) is defined to be:

$$d(i,n-1; m,n) = R^2 d_x \quad (28)$$
$$= \frac{\sin^2\gamma + k^2\cos^2\gamma}{\sin^2\phi} \Delta x$$

where $d_x = \Delta x$ when one grid increment is considered in the x direction. For potential failure paths where the indices i and m differ by no more than one from each other, the result given by Equation (28) is sufficient. For the more general case where the potential failure path goes through more than one elementary region of the data point grid the angle $\theta$ and hence $\gamma$ are not assumed constant along the path. This case is handled by splitting the path into $|m-i|$ segments and using an interpolated value for angle $\theta$ obtained from the measured angles at the nearest grid points.

The more general result for $|m-i| > 0$ is:

$$d(i,n-1; m,n) = \frac{\Delta x}{|m-i|\sin^2\phi} \sum_{j=1}^{|m-i|} (\sin^2\gamma_j + k^2\cos^2\gamma_j) \quad (29)$$

where $\gamma_j = \phi - \theta_j$ is the angle for the $j^{th}$ path segment.

Figure 21:
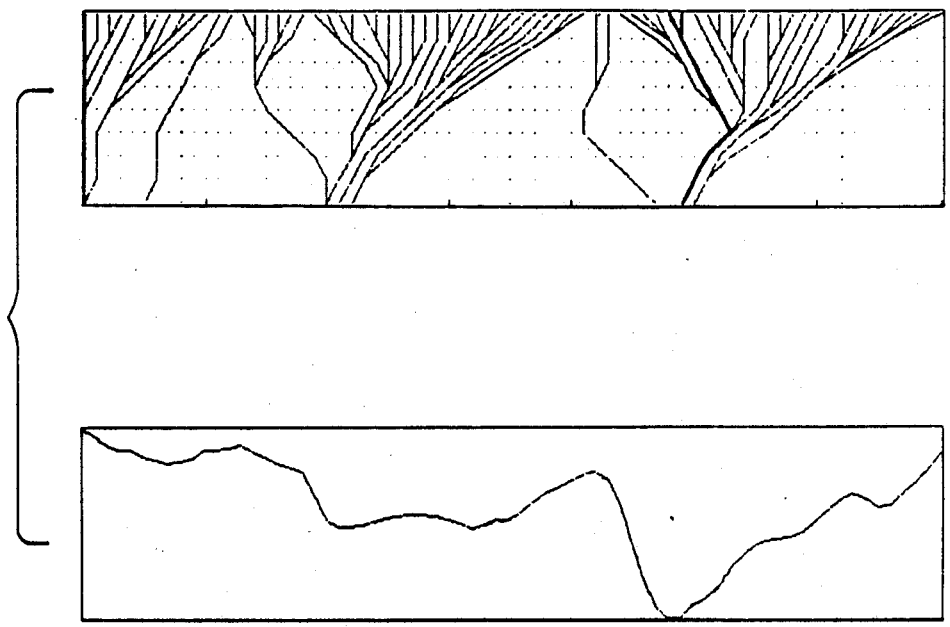
FIG. 21 shows plots of potential failure path and a failure distance versus path ending point, illustrating search model results for specimen A.

FIG. 21 illustrates potential failure paths and failure distances to each edge point along one edge for the lumber specimen A. The heavy line shows the path giving smallest failure distance.

PROCEDURAL VARIATIONS

Figure 22:
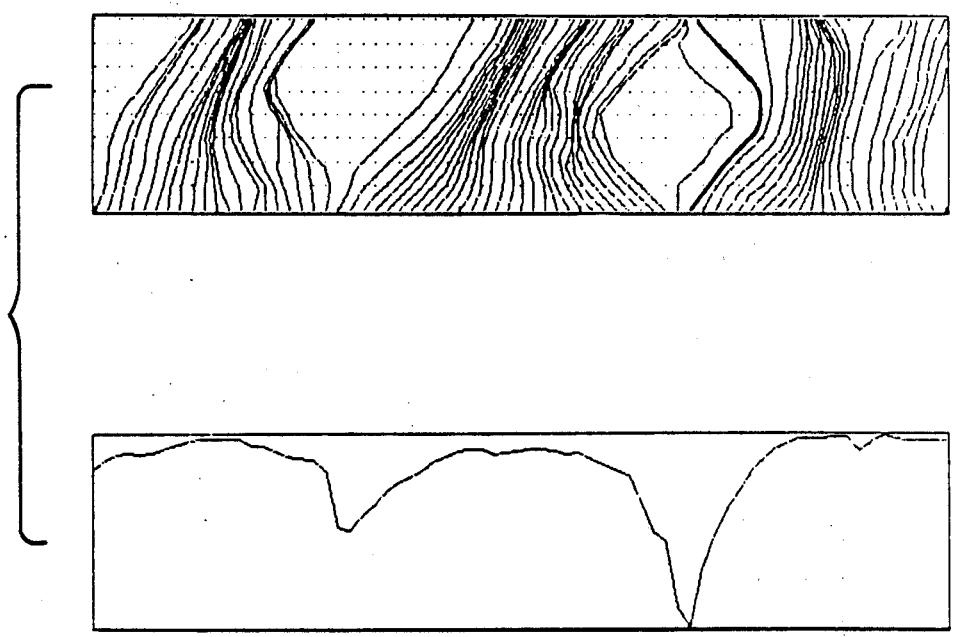
FIG. 22 shows plots similar to FIG. 18, with a grain angle threshold $\theta_t=25°$ and failure distance weighting $(L/x)^2$.

There appears to be justification for reducing the failure distance increments even further than the models specify if the grain angle $\theta$ exceeds some threshold. In some cases, for example, knots are loose or absent, and a failure path should not be credited with any failure distance through those areas. Allowance for this can be accomplished by adjusting the failure distance increments to zero for those path increments that have grain angle magnitude $|\theta| > \theta_t$ where $\theta_t$ is a threshold value to be chosen. FIGS. 22 and 23 illustrate the results of implementing the ellipsoidal and search models respectively with $\theta_t$ set to 25° for lumber specimen A.

Figure 26:
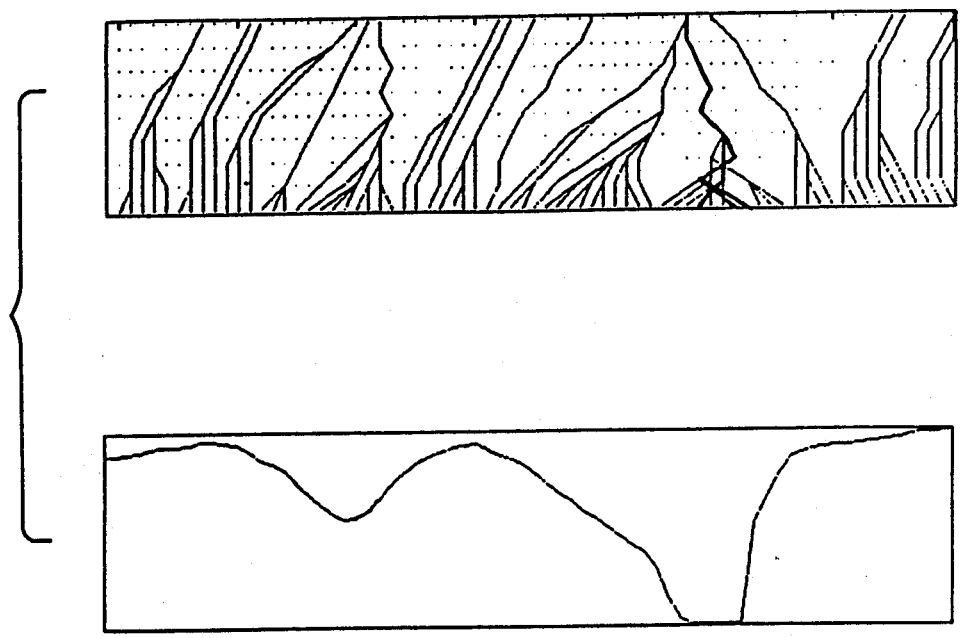
FIG. 26 shows plots of potential failure paths and failure distance versus path ending point, illustrating search model results for specimen A with a grain angle threshold $\theta_t=25°$, the failure path ending points being at the opposite edge from those illustrated in FIG. 23.
Figure 37:
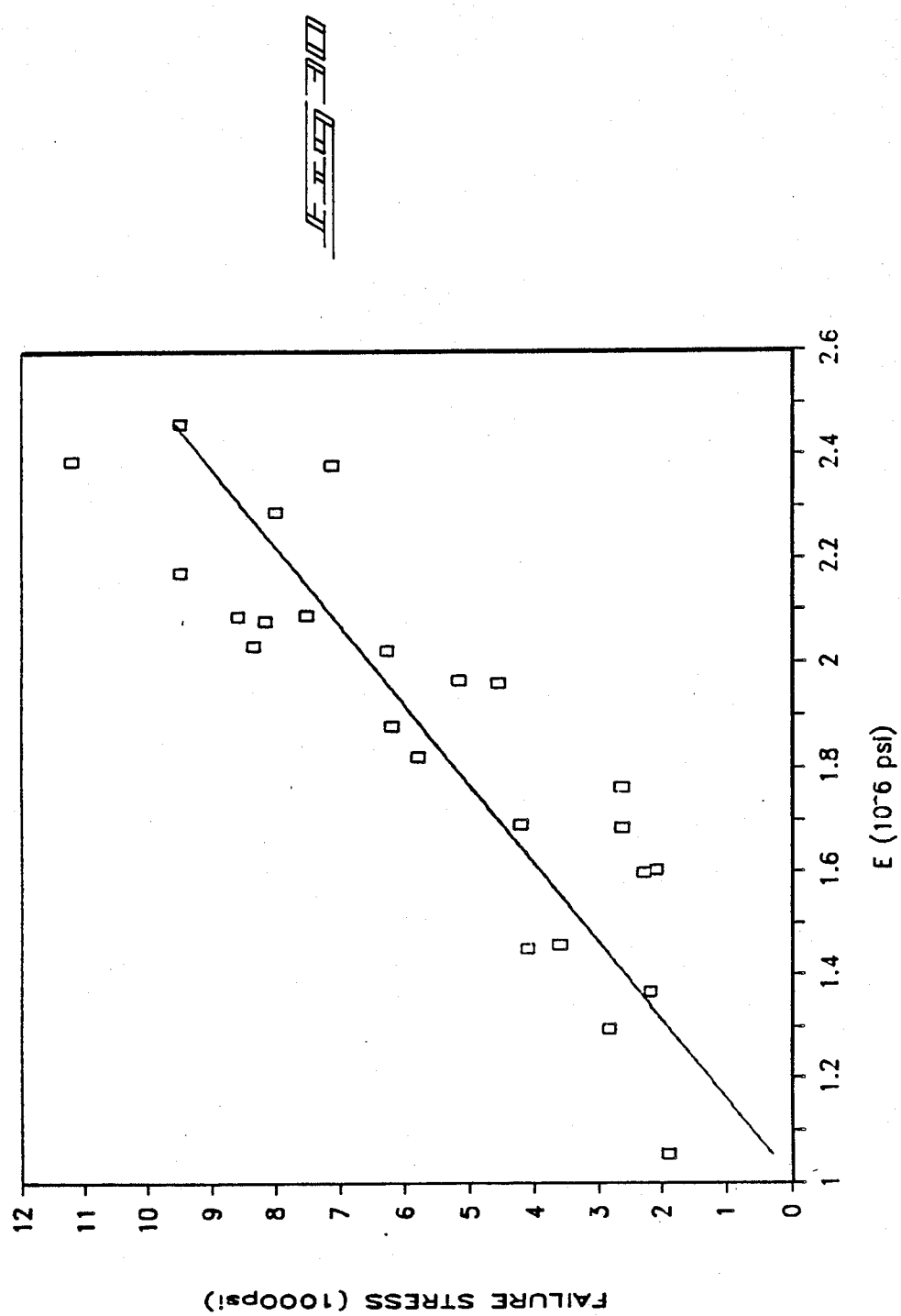
Figure 24:
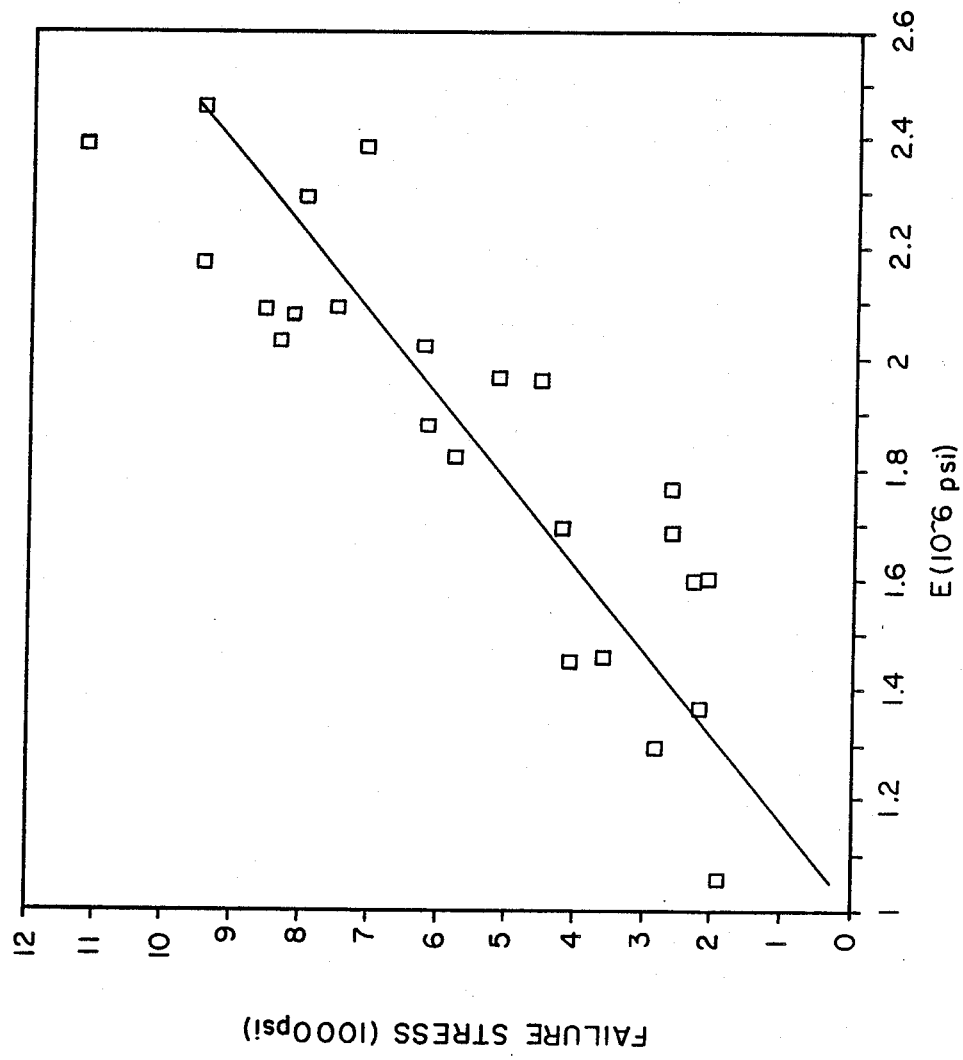
FIG. 24 shows plots of potential failure paths and failure distance versus path starting points, illustrating ellipsoidal model results for specimen A with grain angle threshold $\theta_t=25°$ and failure distance weighting $(L/x)^2$, the failure paths starting at points at the opposite edge of the specimen from those shown in FIG. 22.

A natural point to investigate is the difference that might result if one were to start at the other lumber edge in the forward-directed failure path definition for the ellipsoidal model or to end at the other edge in the backward-directed failure path definition for the search model. FIG. 24 shows results for the ellipsoidal model with $\theta_t=25°$ as in FIG. 22 but with failure paths starting from the other edge. FIG. 26 gives the comparison for the search model with $\theta_t=25°$, as in FIG. 23, but with failure paths ending at the other edge. Some differences are observed in the results depending on the starting or ending edge for the failure paths.

There is evidence that tensile strength is more dependent on local grain angle at the edges of the lumber than in the center. Consequently, some weighting of the distance measure with position in the piece may be important. For example, one edge weighting function of position x across the lumber could be:

$$h(x) = \frac{1}{2\tau} \frac{\cos h((x - a/2)/\tau)}{\sin h(a/(2\tau))} \quad (30)$$

where "a" is the width of the piece and $\tau$ is a shape constant for the weighting function. The function h(x) has a hyperbolic cosine shape with a constant multiplier required to make it integrate to 1 across the piece width.

If the edge is weighted twice as heavily as the center, then $\tau=0.3797a$ and the function becomes:

$$h(x)=(0.760346/a) \cos h(1.316958(2x/a-1)) \quad (31)$$

Figure 25:
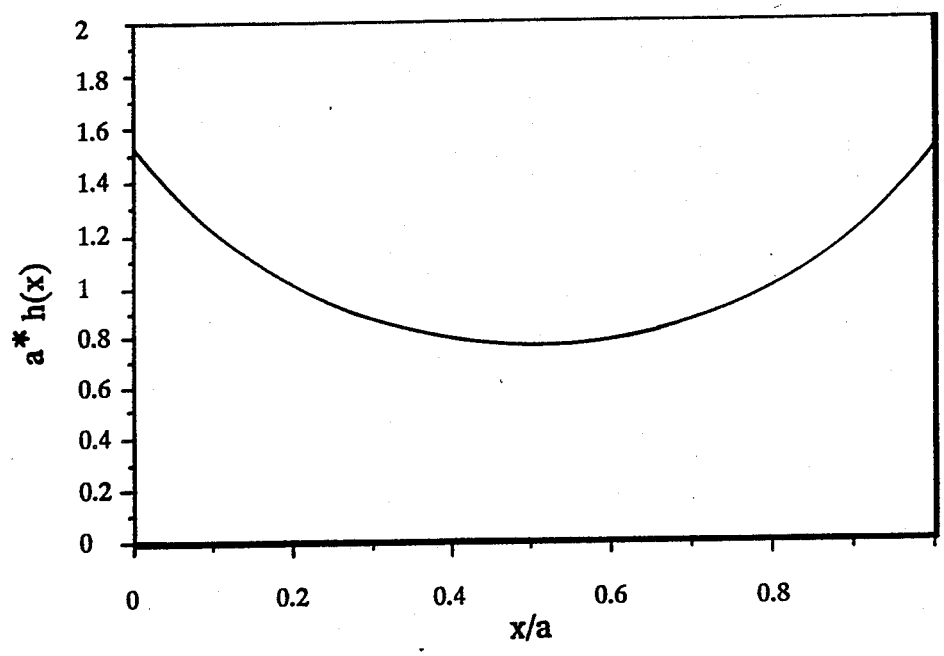
FIG. 25 illustrates a plot of the normalized curve for failure distance versus the normalized variable for the position x across a specimen. The area under the curve is equal to 1, and the shape constant has been chosen so that the value in the center is ½ the value at the lumber edges.

FIG. 25 is a plot of the weighting function in Equation (31), and FIG. 27 is the result of using the weighting function of Equation (31) with the ellipsoidal model applied to specimen A as in FIG. 22. FIG. 28 is the result of using it with the search model on specimen A as in FIG. 23.

TRACKS MODEL

From observation of pieces tested for the present work and previously, it is clear that lumber often fails in tension along a considerable length. A typical failure will occur partially through a cross-section with an edge knot, then along the length to another cross-section with local grain angle problem, where the failure is completed. The tracks model was developed to account for these types of failures with reasonable processing time requirements.

The tracks model was developed by defining N measurement tracks arranged geometrically about a board, each consisting of a row of measurement grid points (N=9 was used). At any set of corresponding points along the tracks, N corresponding numbers are maintained, each one defined as the track failure distance at that group of points. The failure distance at each group of corresponding points is the combination of the track failure distances at the corresponding point locations. The failure strength estimate for the piece of lumber is then proportional to the lowest failure distance for any group of corresponding points along the tracks.

The tracks model can be graphically seen in FIG. 29, which illustrates failure distances along board specimen A, plus a combination of the failure distances as described below.

The track failure distance $D_x(z)$ for the track at position x and cross-section at position z along the lumber is defined as:

$$D_x(z) = (1-\alpha)D_x(z - \Delta z) + \alpha d_x(z), \quad \text{if } d_x(z) \geq D_x(z - \Delta z)$$
$$= d_x(z), \text{ otherwise}$$

where
 $D_x(z-\Delta z)$ is the track failure distance at a cross-section $\Delta z$ upstream from z,
 $d_x(z)$ is a failure distance value computed from the grain angle at position (z,x) only, and
 $\alpha$ is a memory weighting constant.

The track failure distance $D_x(z)$ is a weighted average of the upstream values $d_x(u)$ for $u \leq z$ with the most recent value $d_x(z)$ being weighted most heavily with constant $\alpha$, the next most recent value with constant $\alpha(1-\alpha)$, the next with $\alpha(1-\alpha)^2$, etc. This is an exponential weighting given approximately by $\exp(-\alpha(z-u)/\Delta z)$ of upstream values $d_x(u)$. However, if the present value $d_x(z)$ is less than the history (upstream value $D_x(z-\Delta z)$), then the value $D_x(z)$ is set to $d_x(z)$.

This definition of $D_x(z)$ allows the affect of weak areas to be felt immediately and yet gives a mechanism for this weakness to be "forgotten" after enough distance has passed. The value for $\alpha$ determines the "distance constant" $\Delta z/\alpha$ where the contribution from the weak point has dropped to $1/e=0.37$ of its initial value.

The value $d_x(z)$ for the illustrative example disclosed here was determined from Hankinson's formula as:

$$d_x(z) = \frac{k^2}{k^2\cos^2\theta + \sin^2\theta} \Delta x$$

where $\theta$ is the grain angle at (z,x).

TEST RESULTS 24 pieces of 2×4 Douglas Fir and Larch stud lumber were obtained from a local lumber yard. Some attempt was made to select pieces that appeared to be more or less uniform in the edge (y) direction. Also, pieces were selected that would appear most likely to fail in tension in a 70 cm length near the center of the piece. Then, the tensile testing results would not as likely be confounded by failure occurring in the grips of the tester. No other special consideration was given to taking the lumber sample other than to try to include some pieces that had examples of local grain characteristics that could induce failure.

First, a 70 cm measurement zone was defined near the center of each piece of lumber; second, three flatwise bending E measurements were made on a simply-supported, center-loaded, 48 inch (122 cm) span with span center spaced at three points along the 70 cm measurement zone; third, each piece was weighed; fourth, grain angle measurements were made on a 8 cm×70 cm laterally centered area of each face and a 2 cm×70 cm laterally centered area of each edge; and finally, the tensile strength of each piece was obtained by tensile testing to failure.

Simple linear regression analyses were performed relating the measured tensile failure stress to the failure distances obtained from the three strength estimation models studied. Table 1 shows the coefficients of determination ($r^2$) obtained from these analyses as well as one relating tensile failure stress to E (the E obtained from the center measurement was used). Note that $r^2=0.77$ for the regression of tensile failure stress on E. FIG. 30 is a scatter plot showing tensile failure stress versus E for the 24 piece sample.

TABLE 1

| | MODEL NAME | COEF. OF DET. ($R^{-2}$) | ACROSS PIECE (X) WEIGHTING CONSTANT | FAIL. DIST. INCREMENT WEIGHTING | ANGLE LIMIT (deg) | MEMORY CONSTANT |
|---|---|---|---|---|---|---|
| 1 | ELLIPS | 0.594 | uniform | L/X | 90 | na |
| 2 | ELLIPS | 0.669 | uniform | $(L/X)^{-2}$ | 90 | na |
| 3 | SEARCH | 0.663 | uniform | $(L/X)^{-2}$ | 90 | na |
| 4 | TRACKS | 0.681 | uniform | hank. | 90 | 0.05 |
| 5 | TRACKS | 0.672 | uniform | hank. | 90 | 0.02 |
| 6 | ELLIPS | 0.580 | uniform | L/X | 25 | na |
| 7 | ELLIPS | 0.671 | uniform | $(L/X)^{-2}$ | 25 | na |
| 8 | SEARCH | 0.507 | uniform | $(L/X)^{-2}$ | 25 | na |
| 9 | TRACKS | 0.656 | uniform | hank. | 25 | 0.05 |
| 10 | TRACKS | 0.650 | uniform | hank. | 25 | 0.02 |
| 11 | ELLIPS | 0.561 | 0.38 width | L/X | 90 | na |
| 12 | ELLIPS | 0.681 | 0.38 width | $(L/X)^{-2}$ | 90 | na |
| 13 | SEARCH | 0.686 | 0.38 width | $(L/X)^{-2}$ | 90 | na |
| 14 | TRACKS | 0.721 | 0.38 width | hank. | 90 | 0.05 |
| 15 | TRACKS | 0.703 | 0.38 width | hank. | 90 | 0.02 |
| 16 | ELLIPS | 0.538 | 0.38 width | L/X | 25 | na |
| 17 | ELLIPS | 0.675 | 0.38 width | $(L/X)^{-2}$ | 25 | na |
| 18 | SEARCH | 0.530 | 0.38 width | $(L/X)^{-2}$ | 25 | na |
| 19 | TRACKS | 0.701 | 0.38 width | hank. | 25 | 0.05 |
| 20 | TRACKS | 0.686 | 0.38 width | hank. | 25 | 0.02 |
| 21 | E | 0.765 | na | na | na | na |

Multiple linear regression analyses were also performed relating tensile failure stress to E and failure distance. Table 2 shows the coefficients of determination obtained from these analyses.

TABLE 2

| | MODEL NAME | COEF. OF DET. ($R^{-2}$) | ACROSS PIECE (X) WEIGHTING CONSTANT | FAIL. DIST. INCREMENT WEIGHTING | ANGLE LIMIT (deg) | MEMORY CONSTANT |
|---|---|---|---|---|---|---|
| 1 | ELLIPS | 0.829 | uniform | L/X | 90 | na |
| 2 | ELLIPS | 0.831 | uniform | $(L/X)^{-2}$ | 90 | na |
| 3 | SEARCH | 0.839 | uniform | $(L/X)^{-2}$ | 90 | na |
| 4 | TRACKS | 0.857 | uniform | hank. | 90 | 0.05 |
| 5 | TRACKS | 0.859 | uniform | hank. | 90 | 0.02 |
| 6 | ELLIPS | 0.846 | uniform | L/X | 25 | na |
| 7 | ELLIPS | 0.837 | uniform | $(L/X)^{-2}$ | 25 | na |
| 8 | SEARCH | 0.841 | uniform | $(L/X)^{-2}$ | 25 | na |
| 9 | TRACKS | 0.852 | uniform | hank. | 25 | 0.05 |
| 10 | TRACKS | 0.854 | uniform | hank. | 25 | 0.02 |
| 11 | ELLIPS | 0.827 | 0.38 width | L/X | 90 | na |
| 12 | ELLIPS | 0.829 | 0.38 width | $(L/X)^{-2}$ | 90 | na |
| 13 | SEARCH | 0.845 | 0.38 width | $(L/X)^{-2}$ | 90 | na |
| 14 | TRACKS | 0.871 | 0.38 width | hank. | 90 | 0.05 |
| 15 | TRACKS | 0.870 | 0.38 width | hank. | 90 | 0.02 |
| 16 | ELLIPS | 0.832 | 0.38 width | L/X | 25 | na |
| 17 | ELLIPS | 0.834 | 0.38 width | $(L/X)^{-2}$ | 25 | na |
| 18 | SEARCH | 0.848 | 0.38 width | $(L/X)^{-2}$ | 25 | na |
| 19 | TRACKS | 0.867 | 0.38 width | hank. | 25 | 0.05 |
| 20 | TRACKS | 0.866 | 0.38 width | hank. | 25 | 0.02 |

The results from the tracks model seemed particularly encouraging, so the test effort was manipulated in that direction by incorporating data from the other face and the edges. This data was then combined in the following five different ways to obtain data for combination tracks.

1. The measured angle from each point on each of the top 9 face tracks was combined with the measured angle from the point immediately below it on the bottom face. The resulting new angles were used to compute the $d_x(z)$ values for 9 tracks. In the case of the face tracks nearest the edges, the nearest center edge track data was also included. The combination method was to choose, from among the data to be combined, the angle having largest magnitude. Each $d_x(z)$ value was multiplied by the weighting function of Equation (31) to give the tracks nearest the edge more credit, and this result was used to update the track failure distance $D_x(z)$.

2. The $d_x(z)$ values were computed for all top and bottom face measurement grid points and averaged pairwise top and bottom to give new $d_x(z)$ values for 9 tracks. Computation of $D_x(z)$ utilized these new $d_x(z)$ values and the weighting function of Equation (31) as in Method 1.

3. The $d_x(z)$ values and $D_x(z)$ were computed for each of the 9 tracks on each face for a total of 18 tracks. The tracks were weighted according to Equation (31) to compute failure distance.

4. Same as 3 except the center tracks on each edge of the piece were included for a total of 20 tracks.

5. The $d_x(z)$ values and $D_x(z)$ were computed for tracks 1 and 7 on both the top and bottom faces (four tracks) and equally weighted to compute failure distance. This method is one which operates on a much reduced data set; consequently, it is more implementable.

Using the tracks model with data from more than one face, simple linear regression analyses of tensile failure stress on failure distance were performed for each of the five methods described. Multiple linear regressions where E is included as an independent variable were also performed. Table 3 contains $r^2$ values for both the simple and the multiple regressions. Note that the simple regression $r^2$ values are now above the value 0.77 for the case where E is the only independent variable.

TABLE 3

| MULTIPLE SURFACE PROCESSING METHOD | SIMPLE REGRESSION COEF. OF DET. ($R^{-2}$) | MULT. REGRESSION INCLUDING E COEF. OF DET. ($R^{-2}$) |
|---|---|---|
| 1 | 0.776 | 0.899 |
| 2 | 0.788 | 0.890 |
| 3 | 0.815 | 0.900 |
| 4 | 0.831 | 0.914 |
| 5 | 0.815 | 0.908 |

Figure 32:
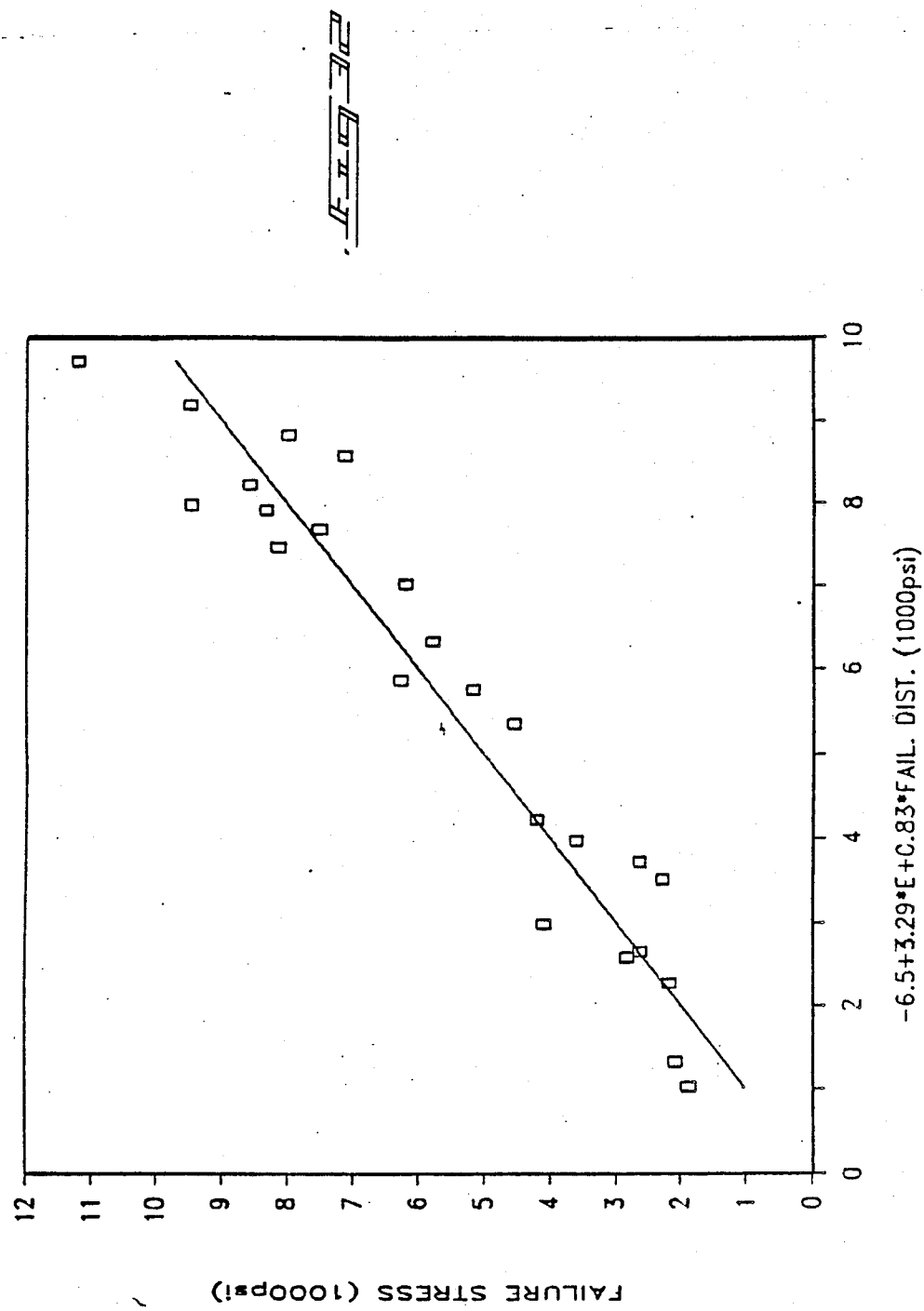
FIG. 32 shows a scatter plot of tensile failure stress versus estimated failure stress from multiple regression on failure distance and E.

The best multiple regression result ($r^2=0.91$) occurred for independent variable E and failure distance from Method 4 above. This result used the hyperbolic function of Equation (31) to weight the track failure distances depending on their position across the piece. FIG. 31 is a scatter plot of tensile failure stress versus the failure distance measure resulting from processing Method 4. FIG. 32 is a scatter plot of tensile failure stress versus estimated failure stress, using the same failure distance measure as in FIG. 31, as well as E.

It is reasonable to make some adjustments in the model to search for the one giving the best estimates of failure stress. However, for the initial small 24 board sample size, there is a danger in carrying this process too far. Given the available data, one could, by carefully defining the strength estimator, exactly predict the observed failure stresses with the estimator—at least this prediction could be made for the specimens in the tested set of boards.

The real test is to apply the model to an independent sample of lumber specimens. Six additional lumber specimens were selected and measured with the same nondestructive procedures as before. Then, just four tracks of measured data were used, along with the regression coefficients from the simplified method described in tracks method 5 to estimate failure stress. Estimated failure stress was compared with actual failure stress obtained by testing the lumber to failure to tension as before. These results are illustrated in Table 4:

TABLE 4

| Specimen # | Estimated Failure Stress (ksi) | Actual Failure Stress ksi |
|---|---|---|
| 1 | 3.30 | 3.44 |
| 2 | 4.05 | 3.27 |
| 3 | 3.02 | 1.97 |
| 4 | 3.06 | 2.11 |
| 5 | 3.46 | 1.92 |
| 6 | 2.74 | 2.28 |

The variance of the error between estimated and actual failure stress for the above six specimens is computed to be 0.863 ksi$^2$. From the original 24 piece sample, the sample variance of failure stress is 7.87 ksi$^2$. If the estimator using E and failure distance removes 90% of the variance, then the residual variance should be $(0.1)(7.87 \text{ ksi}^2)=0.787$ ksi$^2$, which for this small sample is consistent with the observed value 0.863 ksi$^2$.

It is interesting that in the process of gathering data from the grain angle indicator, one piece showed very high grain angles (8° to 10°) all along the face of the piece for no apparent reason. No problem was found with the equipment. When the piece was turned over and measured about the other face, similar values were observed, but with negative sign. Excessive general grain angle would not have been observed by visual grading of this piece, but it became very evident after tensile testing, when failure occurred along the direction of the excessive grain angle. Failure stress of this piece was 2828 psi and E was $1.30 \times 10^6$ psi.

Excellent results (highest $r^2=0.83$) for regression of tensile failure stress on failure distance were obtained, and they compare favorably with the value 0.77 for the previous generally recognized best nondestructive measurement E for strength. When E and failure distance are both used in multiple regression analysis for strength estimation, $r^2$ as high as 0.91 is observed. In that case one can say that use of grain angle measurements has removed $(100)(0.91-0.77)/(1-0.77)=61\%$ of the variance remaining after E is used in the strength estimation.

The $r^2=0.77$ value is quite high for the regression of tensile failure stress on E when compared with values reported elsewhere. There are several possible explanations for this. First, this is a short span tensile test and a comparably short span E measurement; consequently, the tests made to date relate for a smaller, more closely defined region of material than for some of the other results reported in the literature. Second, usual statistical procedures for sampling the material were not followed; rather some attempt was made to select material that would allow us to exercise our algorithms for processing grain angle data. It is possible that this selection procedure could have caused a bias in the tensile failure stress versus E regression. Third, the sample size of 24 is quite small.

Limited study of reduced data collection methods for the tracks model indicates that it may function quite well from a much reduced data set.

Some investigation of different parameter values in the failure distance measures was accomplished; however, optimization has definitely not been achieved.

For a small sample of six specimens, the error between estimated and actual tensile failure stress had sample variance consistent with 10% of the sample variance of the unconditional tensile failure stress distribution for the training sample of 24 pieces.

The results presented in this effort show conclusively for the first time that grain angle measurements are useful in reducing the variance of tensile strength estimators for dimension lumber. For the limited sample of 24 specimens studied, it appears that taken singly, failure distance obtained from grain angle measurements is a better estimator for lumber failure stress than is E. In combination, E and failure distance appear to offer a major improvement in tensile strength estimation. Further, the model showing the best results (tracks) promises to be the most easily implementable of the models studied.

In compliance with the statute, the invention has been described in language more or less specific as to structural features. It is to be understood, however, that the invention is not limited to the specific features shown, since the means and construction herein disclosed comprise a preferred form of putting the invention into effect. The invention is, therefore, claimed in any of its forms or modifications within the proper scope of the appended claims, appropriately interpreted in accordance with the doctrine of equivalents.

We claim:

1. A method for nondestructively testing wooden boards, comprising the following steps:
   measuring grain angle values at measurement points in a geometric pattern about each board;
   applying matching functions to the measured grain angle values, wherein the matching functions identify locations on the boards having grain angle values of the same sign in diagonally opposed quadrants about a measurement point and grain angle values of opposite signs in adjacent quadrants; and
   physically processing the individual boards as a function of the identified locations.

2. The method of claim 1 wherein the step of applying the matching functions comprises:
   applying the Cauchy-Schwarz inequality to the measured grain angle values and matching functions.

3. A method for nondestructively testing wooden boards, comprising the following steps:
   measuring grain angle values in a geometric pattern about each board;
   transforming the grain angle values measured with respect to each board to extract features indicative of knot identification, grain angle perturbations or strength of the board; and
   physically processing the individual boards as a function of the extracted features;
   wherein the step of transforming the grain angle values comprises:
   applying an ellipsoidal model to the measured grain angle values to define a series of potential failure paths for selecting path segments having minimum failure distances starting at incremental points along one edge of a board surface and ending at its opposite edge;
   calculating a failure distance for each path as the sum of incremental failure distances for segments along the path;
   selecting the potential failure path having minimum failure distance; and
   assigning a strength value to each board as a function of the failure distance along the selected potential failure path.

4. A method for nondestructively testing wooden boards, comprising the following steps:
   measuring grain angle values in a geometric pattern about each board;
   transforming the grain angle values measured with respect to each board to extract features indicative of knot identification, grain angle perturbations or strength of the board; and
   physically processing the individual boards as a function of the extracted features;
   wherein the step of transforming the grain angle values comprises:
   applying a search model to the measured grain angle values to define a series of potential failure paths starting at incremental points along one edge of a board surface and ending at its opposite edge by selecting path segments such that the cumulative failure distance for each path is minimized;
   calculating a failure distance for each path as the sum of incremental failure distances or segments along the path;
   selecting the potential failure path having minimum failure distance; and
   assigning a strength value to each board as a function of the failure distance along a selective potential failure path.

5. A method for nondestructively testing wooden boards, comprising the following steps:
   measuring grain angle values in a geometric pattern about each board;
   transforming the grain angle values measured with respect to each board to extract features indicative of knot identification, grain angle perturbations or strength of the board; and
   physically processing the individual boards as a function of the extracted features;
   wherein the step of transforming the grain angle values comprises:
   applying a tracks model to the measured grain angle values along a plurality of preselected geometric tracks about a board to define failure distances at geometrically corresponding locations along each track;
   combining the corresponding failure distances for the plurality of tracks; and
   assigning a strength value to each board as a function of the minimum combined failure distances for the plurality of paths.

6. The method of claim 5 wherein the failure distance $D_x(z)$ along each track at position z along a board is defined as:

$$D_x(z) = (1 - \alpha)D_x(z - \Delta z) + \alpha d_x(z), \quad \text{if } d_x(z) \geq D_x(z - \Delta z)$$
$$= d_x(z), \text{ otherwise}$$

where
   $D_x(z - \Delta z)$ is the track failure distance at a cross-section $\Delta z$ upstream from z,
   $d_x(z)$ is a failure distance value computed from the grain angle at position (z,x) only, and
   $\alpha$ is a memory weighting constant.

7. An apparatus for nondestructively testing wooden boards, comprising:
   grain angle indicator means for measuring grain angle values in a geometric pattern about each board;
   transport means for providing relative movement between each board and the grain angle indicator means as the surfaces of the board is being scanned;
   computer means connected to the grain angle indicator means for applying matching functions to the measured grain angle values, wherein the matching functions identify locations on the boards having grain angle values of the same sign in diagonally opposed quadrants about a measurement point and grain angle values of opposite signals in adjacent quadrants; and
   grader means connected to the computer means for physically processing the individual boards as a function of the identified locations.

8. The apparatus of claim 7 wherein the computer means is programmed to apply the Cauchy-Schwarz inequality to the measured grain angle values and matching functions.

9. An apparatus for nondestructively testing wooden boards, comprising:
   grain angle indicator means for measuring grain angle values in a geometric pattern about each board;

transport means for providing relative movement between each board and the grain angle indicator means as the surface of the board is being scanned;

computer means connected to the grain angle indicator means for transforming the grain angle values measured with respect to each board to extract features indicative of knot identification, grain angle perturbations or strength of the board; and grader means connected to the computer means for physically processing the individual boards as a function of the identified extracted features;

wherein the computer means is programmed to apply an ellipsoidal model to the measured grain angle values to define a series of potential failure paths for selecting path segments having minimum failure distances starting at incremental points along one edge of a board surface and ending at its opposite edge;

calculating a failure distance for each path as the sum of incremental failure distances for segments along the path;

selecting the potential failure path having minimum failure distance; and wherein the grader means includes means for assigning a strength value to each board as a function of the failure distance along the selected potential failure path.

10. An apparatus for nondestructively testing wooden boards, comprising:

grain angle indicator means for measuring grain angle values in a geometric pattern about each board;

transport means for providing relative movement between each board and the grain angle indicator means as the surface of the board is being scanned;

computer means connected to the grain angle indicator means for transforming the grain angle values measured with respect to each board to extract features indicative of knot identification, grain angle perturbations or strength of the board; and grader means connected to the computer means for physically processing the individual boards as a function of the identified extracted features;

wherein the computer means is programmed to apply a search model to the measured grain angle values to define a series of potential failure paths starting at incremental points along one edge of a board surface and ending at its opposite edge by selecting path segments such that the cumulative failure distance for each path is minimized;

calculating a failure distance for each path as the sum of incremental failure distances or segments along the path;

selecting the potential failure path having minimum failure distance; and wherein the grader means includes means for assigning a strength value to each board as a function of the failure distance along a selective potential failure path.

11. An apparatus for nondestructively testing wooden boards, comprising:

grain angle indicator means for measuring grain angle values in a geometric pattern about each board;

transport means for providing relative movement between each board and the grain angle indicator means as the surface of the board is being scanned;

computer means connected to the grain angle indicator means for transforming the grain angle values measured with respect to each board to extract features of knot identification, grain angle perturbations or strength of the board; and grader means connected to the computer means for physically processing the individual boards as a function of the identified features;

wherein the computer means is programmed to apply a tracks model to the measured grain angle values along a plurality of preselected geometric tracks about a board to define failure distances at geometrically corresponding locations along each track;

combining the corresponding failure distances for the plurality of tracks; and wherein the grader means includes means for assigning a strength value to each board as a function of the minimum combined failure distances for the plurality of paths.

12. The apparatus of claim 11 wherein the computer means is programmed to define the failure distance $D_x(z)$ along each track at position z along a board as:

$$D_x(z) = (1 - \alpha)D_x(z - \Delta z) + \alpha d_x(z), \quad \text{if } d_x(z) \geq D_x(z - \Delta z)$$
$$= d_x(z), \text{ otherwise}$$

where
$D_x(z - \Delta z)$ is the track failure distance at a cross-section z upstream from z.

$d_x(z)$ is a failure distance value computed from the grain angle at position (z,x) only, and $\alpha$ is a memory weighting constant.

13. An apparatus for nondestructively testing wooden boards, comprising:

grain angle indicator means for measuring grain angle values at measurement points in a geometric pattern about each board;

transport means for providing relative movement between each board and the grain angle indicator means as the surface of the board is being scanned;

computer means connected to the grain angle indicator means for identifying a grain angle field whose values at the grain angle measurement points are vectors of equal magnitude having angles that are a function of the measured grain angle at those points and extracting features of the vector field that identify structural quality of the board by vector analysis; and grader means connected to the computer means for physically processing the individual boards as a function of the extracted features.

14. The apparatus of claim 13 wherein the computer means is programmed to determine curl of the vector field.

15. The apparatus of claim 13 wherein the computer means is programmed to determine divergence of the vector field.

16. The apparatus of claim 13 wherein the computer means is programmed to determine a gradient magnitude function of the vector field.

17. The apparatus of claim 16 wherein the computer means is further programmed to determine the gradient magnitude as a function of curl and divergence of the vector field.

18. The apparatus of claim 16 wherein the computer means is further programmed to determine the gradient magnitude as the square root of the sum of the square of the magnitude of curl plus the square of divergence of the vector field.

19. A method for nondestructively testing wooden boards, comprising the following steps:
- measuring grain angle values at measurement points in a geometric pattern about each board;
- identifying a grain angle vector field whose values at the grain angle measurement points are vectors of equal magnitude having angles that are a function of the measured grain angle at the measurement points;
- extracting features of the vector field that identify structural quality of the board by vector analysis; and
- physically processing the board as a function of the extracted features.

20. The method of claim 19 wherein the step of extracting features includes computing the curl of the vector field.

21. The method of claim 19 wherein the step of extracting features includes computing the divergence of the vector field.

22. The method of claim 19 wherein the step of extracting features includes computing a gradient magnitude function of the vector field.

23. The method of claim 22 wherein the gradient magnitude function is determined as a function of curl and divergence of the vector field.

24. The method of claim 22 wherein the gradient magnitude function is calculated as the square root of the sum of the square of the magnitude of curl plus the square of divergence of the vector field.

* * * * *

UNITED STATES PATENT AND TRADEMARK OFFICE
CERTIFICATE OF CORRECTION

PATENT NO. : 4,926,350

DATED : May 15, 1990

INVENTOR(S) : Friend K. Bechtel et al.

It is certified that error appears in the above-identified patent and that said Letters Patent is hereby corrected as shown below:

Column 24, line 4 change "selective" to --selected--;

Column 25, line 12 after "to" add a colon (:) and insert --(a)--
Line 19 change "calculating" to --(b) calculate--;
Line 21 after the semicolon (;) add --and--;
Line 22 change "selecting" to --(c) select--;
Line 23 delete "and";
Line 24 delete "wherein"; change "includes" to --further including--;
Line 43 after the word "to" insert a colon (:) and insert --(a)--
Line 50 change "calculating" to --(b) calculate--;
Line 52 after the semicolon (;) insert "and";
Line 53 change "selecting" to --(c) select--;
Line 54 delete "and";
Line 55 delete "wherein"; change "includes" to --further including--
Line 57 change "a selective" to --the selected--.

UNITED STATES PATENT AND TRADEMARK OFFICE
CERTIFICATE OF CORRECTION

PATENT NO. : 4,926,350
DATED : May 15, 1990
INVENTOR(S) : Friend K. Bechtel et al It is certified that error appears in the above-identified patent and that said Letters Patent is hereby corrected as shown below:

Column 26, line 6 after the word "to" add a colon (:) and insert --(a)--
Line 10 after the semicolon (;) insert "and";
Line 11 change "combining" to --(b) combine--;
Line 12 delete "and";
Line 13 delete "wherein"; change "includes" to --further including--

Signed and Sealed this

Twenty-second Day of June, 1993

Attest:

MICHAEL K. KIRK

Attesting Officer    Acting Commissioner of Patents and Trademarks